(12) United States Patent
Rajewski et al.

(10) Patent No.: US 8,900,629 B2
(45) Date of Patent: *Dec. 2, 2014

(54) RAPIDLY DISSOLVING PHARMACEUTICAL COMPOSITIONS COMPRISING PULLULAN

(75) Inventors: Roger A. Rajewski, Lawrence, KS (US); Lian G. Rajewski, Lawrence, KS (US); John L. Haslam, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/335,067

(22) Filed: Dec. 22, 2011

(65) Prior Publication Data

US 2013/0005831 A1 Jan. 3, 2013

Related U.S. Application Data

(63) Continuation-in-part of application No. 12/062,727, filed on Apr. 4, 2008, now Pat. No. 8,105,625.

(60) Provisional application No. 60/922,062, filed on Apr. 5, 2007.

(51) Int. Cl.
| | |
|---|---|
| A61K 9/66 | (2006.01) |
| A61K 9/48 | (2006.01) |
| A21D 2/16 | (2006.01) |
| A61K 9/00 | (2006.01) |
| A61K 47/36 | (2006.01) |

(52) U.S. Cl.
CPC ............. *A61K 9/0056* (2013.01); *A61K 9/4816* (2013.01); *A61K 47/36* (2013.01)
USPC ............................ 424/455; 424/452; 426/654

(58) Field of Classification Search
None
See application file for complete search history.

(56) References Cited

U.S. PATENT DOCUMENTS

| | | | |
|---|---|---|---|
| 3,784,390 A | 1/1974 | Hijiya et al. | |
| 3,997,703 A | 12/1976 | Nakashio et al. | |
| 4,623,394 A | 11/1986 | Nakamura et al. | |
| 5,518,902 A | 5/1996 | Ozaki et al. | |
| 6,887,307 B1 | 5/2005 | Scott et al. | |
| 7,267,718 B2 | 9/2007 | Scott et al. | |
| 8,105,625 B2 | 1/2012 | Rajewski et al. | |
| 2003/0072731 A1 | 4/2003 | Gulian et al. | |
| 2003/0107149 A1 | 6/2003 | Yang et al. | |
| 2003/0198674 A1 | 10/2003 | Curatolo et al. | |
| 2003/0211136 A1 | 11/2003 | Kulkarni et al. | |
| 2004/0131661 A1 | 7/2004 | Auffret et al. | |
| 2004/0197410 A1 | 10/2004 | Sugimoto et al. | |
| 2005/0031853 A1 | 2/2005 | Scott et al. | |
| 2005/0249676 A1* | 11/2005 | Scott et al. ................. 424/46 |
| 2006/0018961 A1 | 1/2006 | Nakamura et al. | |
| 2006/0024425 A1 | 2/2006 | Barkalow et al. | |
| 2006/0057207 A1* | 3/2006 | Ziegler et al. ............... 424/484 |
| 2006/0275361 A1 | 12/2006 | Sakanishi et al. | |
| 2007/0042023 A1 | 2/2007 | Puri et al. | |
| 2007/0087036 A1 | 4/2007 | Durschlag et al. | |
| 2007/0087939 A1 | 4/2007 | Cade et al. | |
| 2007/0141137 A1 | 6/2007 | Nagahara et al. | |
| 2007/0196441 A1 | 8/2007 | Auffret et al. | |
| 2008/0248102 A1 | 10/2008 | Rajewski et al. | |
| 2010/0015315 A1* | 1/2010 | Hoffmann et al. ............ 426/534 |

FOREIGN PATENT DOCUMENTS

| | | |
|---|---|---|
| EP | 1072633 | 1/2001 |
| EP | 1580229 | 9/2005 |
| EP | 1593376 | 11/2005 |
| JP | H05-4914 A | 1/1993 |
| JP | 2006-500084 A | 1/2006 |
| JP | 2006-526057 A | 11/2006 |
| WO | WO 00/18365 | 4/2000 |
| WO | 2004006896 A1 | 1/2004 |
| WO | 2004091529 A2 | 10/2004 |
| WO | 2005092968 A1 | 10/2005 |
| WO | WO 2005/105051 | 11/2005 |
| WO | 2006082842 A1 | 10/2006 |
| WO | WO 2008/124617 | 10/2008 |

OTHER PUBLICATIONS

European Search Report for European Application No. 08745143.1, dated Sep. 3, 2012.
Handbook of Pharmaceutical Excipients (Oct. 1988); pp. 123-124.
"NPcaps® Capsules", http://www.capsugel.com/products/npcaps.php; print date Apr. 2008.
Capsugel—NP Caps Website Section Dec. 16, 2004—v01, www.hayashibara-intl.com/pdfs/Pullulanpharma2.pdf; printed Mar. 2012.
"Specifications and Test Methods for Eudragit® L 100-55", Evonik Industries, 2007-09, Info 7.4/E.
"Acryl-Eze® Aqueous Acrylic Enteric System" Technical Data Sheet, Preparation & Use Guidelines by Colorcon; First Publ. Jun. 2001; Revised Mar. 2006.
Benee, "Rapidly Dissolving and Dispersing Films", Journal of Pharmacy and Pharmacology, 55 Supplement (2003), pp. S-70-S-71 (pp. 4).
Stegemann et al., Hard Gelatin Capsules Today—and Tomorrow, dated 2002.
Solutol HS15, Technical Information, BASF, Pharma Ingredients and Services, (Aug. 2010), pp. 1-8.
Li et al., Preparation and Evaluation of Novel Mixed Micelles as Nanocarriers for Intravenous Delivery of Propofol; Nanoscale Research Letters, (2011), 6:275.
International Search Report and Written Opinion mailed Jul. 9, 2008 (PCT/US 08/59447 (WO 08/124617)).
Search Report for related Japanese Patent Application 2010-502327 dated Jan. 22, 2013.

* cited by examiner

*Primary Examiner* — Jeffrey T Palenik
(74) *Attorney, Agent, or Firm* — Merchant & Gould PC

(57) ABSTRACT

The present disclosure provides rapidly dissolving oral capsules and films comprising pullulan, a plasticizer, and a dissolution enhancing agent.

11 Claims, 4 Drawing Sheets

RAPIDLY DISSOLVING PHARMACEUTICAL COMPOSITIONS COMPRISING PULLULAN

CROSS-REFERENCE TO RELATED APPLICATIONS

This application is a continuation-in-part of U.S. patent application Ser. No. 12/062,727, filed Apr. 4, 2008, now U.S. Pat. No. 8,105,625, issued Jan. 31, 2012, which claims the benefit of U.S. Provisional Application No. 60/922,062, Rapidly Dissolving Pharmaceutical Compositions Comprising Pullulan, filed Apr. 5, 2007, the entire contents of each of which is incorporated herein by reference.

BACKGROUND OF THE INVENTION

Oral capsules are a well-known dosage form for administering various agents into the body. Generally speaking, such capsules have two basic components, namely, a fill material that includes a pharmaceutically active agent, and a shell that encapsulates the fill material. Upon administration, the fill material is released and absorbed by the body as the shell degrades under various digestive forces.

Many specific constituents have been used to form the shell of various capsule formulations. One basic component is a matrix, or film forming material, such as gelatin, hydroxypropyl methyl cellulose (HPMC), gums, or other polymeric materials including pullulan. Certain types of pullulan capsules are commercially available, for example, Capsugel NPcaps® capsules are available from Pfizer. Capsugel NPcaps® capsules contain pullulan, carageenan, and potassium chloride.

The present disclosure provides hard pullulan capsules that disintegrate more rapidly than Capsugel NPcaps® capsules in the oral cavity for the rapid delivery of pharmaceutical agents. The disclosure further provides aqueous pullulan film forming compositions with good setting properties to be used in the manufacture of hard capsules in a dip molding process, that disintegrate rapidly in the oral cavity.

BRIEF SUMMARY OF THE INVENTION

In one embodiment, the disclosure provides an orally dissolving capsule comprising pullulan, a plasticizer, a dissolution enhancing agent and a wetting agent. In one aspect, the pullulan is present in an amount from about 60 to about 99 wt % based on total capsule shell solids.

In one aspect, the capsule shell formulation contains a wetting agent selected from Solutol, sorbitan monolaurate, sorbitan monopalmitate, sorbitan monostearate, sorbitan monooleate, lauryl ether, cetyl ether, stearyl ether, oleyl ether, polyoxyethylene (40) stearate, polyoxyethylene (100) stearate, sucrose monolaurate, sucrose stearate, glycerol monostearate, sorbitan monostearate, sorbitan tristearate, sorbitan monopalmitate, poloxamer, oleyl alcohol, octyl glucoside, nonoxynols, glycerol laurate, and vitamin E TPGS. In another aspect, the wetting agent is present in an amount from about 1 to about 10 wt % based on total capsule shell solids. In a specific aspect, the wetting agent is Solutol.

In another aspect, the pullulan capsule shell formulation contains a plasticizer which is a polyol selected from glycerol, propylene glycol, polyvinyl alcohol, sorbitol, pluronic and maltitol. In another aspect, the plasticizer is present in the capsule shell formulation in an amount from about 0.1 to about 20 wt % based on total capsule shell solids.

In a further aspect, the disclosure provides a pullulan capsule shell formulation that contains a dissolution enhancing agent selected from maltose, lactose, sorbitol, mannitol, gluconic acid lactone, xylitol, maltitol, and isomalt. In a specific aspect, the dissolution enhancing agent is selected from at least one of maltose, lactose, and sorbitol. In another aspect, the dissolution enhancing agent is present in an amount from about 0.1 to about 35 wt % based on total capsule shell solids.

In another aspect, the pullulan capsule shell formulation contains up to about 5 wt % each of one or more selected from the group consisting of a sweetener, flavoring agent, and saliva inducing agent, based on total capsule shell solids.

In a further aspect, the disclosure provides a pullulan capsule shell formulation that contains a strengthening agent. The strengthening agent is selected from polydextrose, cellulose, cellulose derivatives, maltodextrin, guar gum, gelatin, alginates, and gum arabic. In a specific aspect, the strengthening agent is polydextrose.

In a preferred aspect, the disclosure provides an orally dissolving capsule comprising pullulan, having an average normalized average breakthrough time of less than 30 seconds in an aqueous disintegration test at 37° C.

In a specific aspect, the disclosure provides an orally dissolving capsule comprising about 70-80 wt % pullulan, about 5-10 wt % glycerin, about 5-10 wt % polydextrose, about 2-10 wt % maltose, about 1-5 wt % sorbitol and about 1-5 wt % Solutol, based on the total weight of the capsule shell solids.

In another embodiment, the disclosure provides an orally dissolving film comprising pullulan, a plasticizer, a dissolution enhancing agent and a strengthening agent. In one aspect, the plasticizer is selected from at least one of the group consisting of glycerin, propylene glycol, polyvinyl alcohol, sorbitol, pluronic and maltitol. In another aspect, the dissolution enhancing agent is selected from at least one of the group consisting of maltose, lactose, sorbitol, mannitol, gluconic acid lactone, xylitol, maltitol, and isomalt. In a further aspect, the strengthening agent is selected from at least one of the group consisting of polydextrose, cellulose, cellulose derivatives, maltodextrin, guar gum, gelatin, alginates, and gum arabic. In a specific aspect, the orally dissolving pullulan film contains glycerin, polydextrose and maltose.

Also provided is a pharmaceutical composition comprising a hard capsule shell comprising pullulan, one or more plasticizers, and one or more dissolution enhancing agents; wherein the hard capsule shell is filled with a capsule fill formulation comprising one or more pharmaceutical agents and one or more excipients.

DETAILED DESCRIPTION

Figure 1:
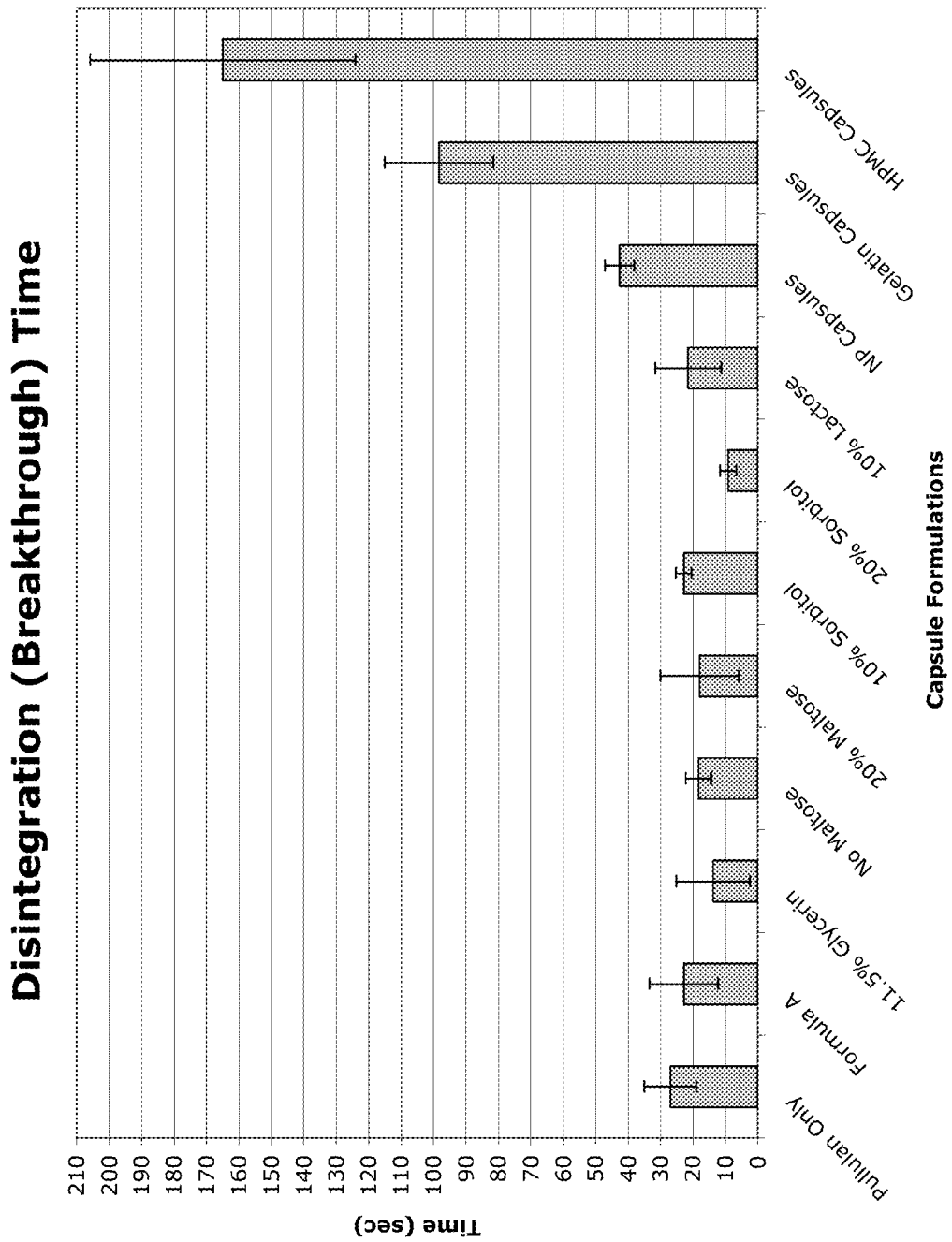
FIG. 1 shows average capsule disintegration times at 37° C. for various capsule formulations.

The present invention is directed to a rapidly dissolving capsule or film receptacle, comprising pullulan, one or more plasticizers, and one or more dissolution enhancing agents. The rapidly dissolving pullulan capsule or film receptacle may be used to rapidly administer one or more pharmaceutical agents to a patient. The invention contemplates that the capsule will contain a therapeutically effective amount of one or more pharmaceuticals in the capsule fill formulation.

The term "therapeutically effective amount" is used to describe an amount of the pharmaceutical that treats, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient and condition, a therapeutically effective amount can be determined by methods known to those of skill in the art.

The term "patient" or "subject" to be treated is preferably a mammal, such as a domesticated animal or a livestock animal. More preferably, the patient is a human.

The term "disintegrate" refers to breaking into parts, or loose cohesion. Thus, a capsule may disintegrate and release its contents prior to entirely dissolving. Disintegration time is equivalent to breakthrough time.

The term "fully dissolve" means to go from a solid state to fully into solution in a liquid. The term "dissolve" may be modified so as to refer to the percent of dissolution; for example, the use of the term "70% dissolved" refers to a capsule shell or film composition that is 30% solid and 70% in solution.

The term "capsule" refers to a hard shell pharmaceutical capsule. The capsule may be amenable to use in capsule filling machine instrumentation for the filling of pharmaceutical drugs and capsule fill formulations. The capsules consist of a body and a cap.

The term "orally dissolving capsule" refers to a capsule that disintegrates in saliva in the oral cavity of a patient with no need for chewing or drinking liquids to ingest the capsule.

Pullulan is a natural, viscous, water-soluble polysaccharide extracellularly produced by growing certain yeasts on starch syrups. Pullulan can be produced through a fermentation process from starch by the fungus *Aureobasidium pullulans*. Specifically, pullulan is a polysaccharide linear polymer consisting of maltotriose units. Three glucose units of maltotriose are connected by an $\alpha$-1,4 glycosidic bond, whereas consecutive maltotriose units are connected to each other by an $\alpha$-1,6 glycosidic bond. Pullulan is an edible, mostly tasteless polymer.

In one aspect, the pullulan has a molecular weight between about 50 to 500 kDa, between about 100 to 400 kDa, between about 150 to 300 kDa, and preferably between about 180 and 250 kDa. In another aspect, the molecular weight is greater than about 50 kDa, greater than about 100 kDa, greater than about 150 kDa, or greater than about 200 kDa.

In one aspect, the hard capsule shell comprises pullulan from about 50 to about 99 wt % of total capsule shell solids. In a further aspect, the receptacle comprises about 60 to 90 wt % pullulan, or 70 to 80 wt % pullulan.

In addition to pullulan, the hard capsule of the present disclosure further comprises one or more plasticizers and one or more dissolution enhancing agents. These additives are included in the shell to control the physical characteristics thereof.

The plasticizing agent is added to control the softness or pliability of the shell. Certain amounts of plasticizing agents are added in order to keep the shell from becoming overly brittle. In one aspect, the plasticizing agent is a polyol that is selected from the group consisting of glycerol, propylene glycol, polyvinyl alcohol, sorbitol, pluronic and maltitol. In a specific aspect, the plasticizer is glycerol. In one aspect the plasticizer is present in the capsule shell at about 0.1% to about 20 wt % of total capsule shell solids. In a specific aspect, the plasticizer is about 5 to about 10 wt % of the capsule shell solids.

The dissolution enhancing agent is added to enhance disintegration, and/or to increase the rate of dissolution, of the capsule or film, in the oral cavity, or in water. The dissolution enhancing agent may be selected form maltose, lactose, sorbitol, gluconic acid lactone, mannitol, xylitol, maltitol, and isomalt. In one aspect, the dissolution enhancing agent is present from about 0.1% to about 35 wt % of the capsule shell solids.

In one aspect, the hard capsule shell optionally further comprises a strengthening agent. The strengthening agent is selected from the group consisting of polydextrose, cellulose, or its derivatives, maltodextrin, guar gum, gelatin, alginates, and gum arabic. The strengthening agent is present from about 0 to about 20 wt % of the weight of the capsule shell. In a specific aspect, the strengthening agent is polydextrose.

In one embodiment, the hard shell capsule containing pullulan further comprises one or more wetting agents. Examples of wetting agents include ethoxylated aliphatic alcohols, polyoxyethylene surfactants, carboxylic esters, polyethylene glycol esters, anhydrosorbitol esters, ethoxylated derivatives of anhydrosorbitol esters, glycol esters of fatty acids, carboxylic amides, monoalkylamine condensates, and polyoxyethylene fatty acid amides.

Specific examples of wetting agents to be used in the capsule shell formulations include, but are not limited to, Solutol (Solutol HS 15, polyoxyl 15 hydroxystearate USP), polysorbate 20 (sorbitan monolaurate), polysorbate 40 (sorbitan monopalmitate), polysorbate 60 (sorbitan monostearate), polysorbate 80 (sorbitan monooleate), Brij 35 (lauryl ether), Brij 58 (cetyl ether), Brij 78 (stearyl ether), Brij 98 (oleoyl ether), Myrj 52 (polyoxyethylene (40) stearate), Myrj 59 (polyoxyethylene (100) stearate), Crodesta SL40 (sucrose monolaurate), sucrose stearate, glycerol monostearate, sorbitan monostearate (SPAN 60), sorbitan tristearate, sorbitan monopalmitate, poloxamer, oleyl alcohol, octyl glucoside, nonoxynols, glycerol laurate, vitamin E TPGS (tocophersolan, alpha-tocophyl polyethylene glycol 1000 succinate), tyloxapol, poloxamers such as PLURONIC™F68, F127, and F108, that are block copolymers of ethylene oxide and propylene oxide, and polyxamines such as TETRONIC™908 (also known as POLOXAMINE™908), that is a tetrafunctional block copolymer derived from sequential addition of propylene oxide and ethylene oxide to ethylenediamine (available from BASF), lecithin, dialkylesters of sodium sulfosuccinic acid such as AEROSOL™OT, that is a dioctyl ester of sodium sulfosuccinic acid (available from American Cyanamid), DUPONOL™P, that is a sodium lauryl sulfate (available from DuPont), TRITON™X-200, that is an alkyl aryl polyether sulfonate (available from Rohm and Haas), TWEEN™ 20 and TWEEN™80, that are polyoxyethylene sorbitan fatty acid esters (available from ICI Specialty Chemicals), Carbowax 3550 and 934, that are polyethylene glycols (available from Union Carbide), Crodesta F-110, that is a mixture of sucrose stearate and sucrose distearate, and Crodesta SL-40 (both available from Croda Inc.), and SA90HCO, that is $C_{18}H_{37}CH_2$ $(CON(CH_3)CH_2$ $(CHOH)_4$ $CH_2OH)_2$. In a specific aspect, the wetting agent is Solutol.

Incorporation of a wetting agent in the capsule shell formulation enhances dissolution and disintegration of the capsules. The hard shell pullulan capsule comprising the wetting agent is slicker when cured, which helps impart ease of handling, ease of processing and improved mouth feel. In another aspect, the pullulan capsules comprising a plasticizer, a dissolution agent and a wetting agent are easier to close, have excellent stability when stored at room temperature, and dissolve rapidly in aqueous environments. In one aspect, 0.1 wt % to 15 wt %; 0.5 wt % to 10 wt %; 1 wt % to 5 wt %; or 1.5 wt % to 3 wt % of wetting agent is employed in the capsule shell formulations, based on the weight of the pullulan in the capsule formulation. In specific aspects, the wetting agent is incorporated at 1 wt %, 1.5 wt %, 2 wt %, 2.5 wt %, 3 wt %, 3.5%, 4 wt %, 4.5 wt %, or 5 wt %, based on the weight of the pullulan in the capsule shell formulation. In a specific aspect, the wetting agent is present at 1.5 wt %, 2 wt %, 2.5 wt % or 3 wt % based on the weight of the pullulan in the capsule shell formulation.

In a specific aspect, the hard shell capsule formulation comprising pullulan, a plasticizer, and a dissolution agent further comprises Solutol as the wetting agent. Solutol (Solutol® HS 15, BASF; macrogol (15)-hydroxystearate, polyethylene glycol 15-hydroxy stearate; polyoxyethylated 12-hydroxystearic acid; Octadecanoic acid, 12-hydroxy-, polymer with alpha-hydro-omega-hydroxypoly(oxy-1,2-ethanediyl)) is a nonionic surfactant that can be used as a solubilizer, or emulsifier. A small part of the 12-hydroxy group can be esterified with polyethylene glycol. It is used in the pharma industry in various injection formulations. Solutol is soluble in water to form clear solutions. Its solubility in water decreases with increasing temperature. In one aspect, the disclosure provides formulations for preparation of pullulan capsules comprising a plasticizer, a dissolution agent and Solutol to impart improved integrity to the capsule shell. In a specific aspect, the wetting agent is Solutol and the dissolution enhancing agent is sorbitol. In another aspect, the wetting agent is Solutol and the plasticizer is glycerin. In another aspect the wetting agent is Solutol and the strengthening agent is polydextrose.

In one aspect, the hard capsule shell optionally further comprises one or more sweeteners. The sweetener may be selected from a solid natural or synthetic sweetener. The natural sugar may be selected from sucrose, dextrose, fructose, lactose, maltose, glucose syrup, invert sugar, and hydrolyzed lactose. The synthetic sweetener may be selected from aspartame, a cyclamate, saccharin, acesulfame salts, neohesperidin dihydrochalcone, sucralose, alitame, astevia, talin, glcyrrhizin, thaumatin, xylitol, and mixtures thereof. The term saccharin as used herein includes saccharin itself, saccharin acids, and saccharin salts such as sodium saccharin. In one aspect, the sweetener is acesulfame K. The sweetener is present from about 0 to about 5 wt % of the weight of the capsule shell.

In one aspect, the hard capsule shell optionally further comprises one or more flavoring agents. The flavoring agents that may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including, without limitation, lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. The flavor is present from about 0 to about 5% by weight of the capsule shell solids.

In one aspect, the hard capsule shell optionally further comprises one or more saliva stimulating agents. One or more salivary stimulants can be optionally added to the capsule shell. Several salivary stimulants are described in U.S. Pat. No. 4,820,506, which is incorporated herein by reference. Salivary stimulants include, but are not limited to, certain organic acids, and sweeteners. Organic acid salivary stimulants include adipic, ascorbic, citric, fumaric, lactic, malic and tartaric acids. Preferred organic acids are citric, malic and ascorbic acids. The most common sweeteners for use as saliva stimulating agents are sugars such as glucose, dextrose, fructose, lactose, maltose, xylose, sucrose, corn sugar syrup, and other sweet mono- or di-saccharides, as well as artificial sweeteners such as acesulfame, aspartame, saccharin, as well as xylitol and other polyols. Preferred sweeteners that are known to be used as salivary stimulants include maltose, acesulfame, aspartame and saccharin. The amount of saliva stimulating agent in the capsule shell is from about 0 to about 15 wt %. In a one aspect, the saliva stimulating agent is present from about 0.1 wt % to about 5 wt % of the weight of the capsule shell.

In one aspect, the hard capsule shell optionally further comprises one or more colorants and opacifiers. Colorants include such compounds as, by way of example and without limitation, titanium dioxide, talc, FD&C Red No. 3, FD&C Red No. 20, FD&C Yellow No. 6, FD&C Blue No. 2, FD&C Green No. 5, FD&C Orange No. 5, FD&C Red No. 8, caramel, ferric oxide, other FD&C dyes, lakes, and natural coloring agents such as grape skin extract, beet red powder, beta-carotene, annato, carmine, turmeric, paprika, and other materials known in the art. The amount of coloring agent used will vary as desired.

Opacifiers include compounds used to render a coating opaque. An opacifier may be used alone or in combination with a colorant. Such compounds include, by way of example and without limitation, titanium dioxide, talc and other materials known in the art.

In one aspect, the pullulan capsule formulation exhibits rapid disintegration and dissolution in saliva in the oral cavity of a patient for rapid delivery of a pharmaceutical agent. Such a capsule provides a platform for the delivery of drugs without having to swallow or consume a glass of water. In one aspect, the capsule disintegrates in the oral cavity of a patient in less than 30 seconds.

Figure 2:
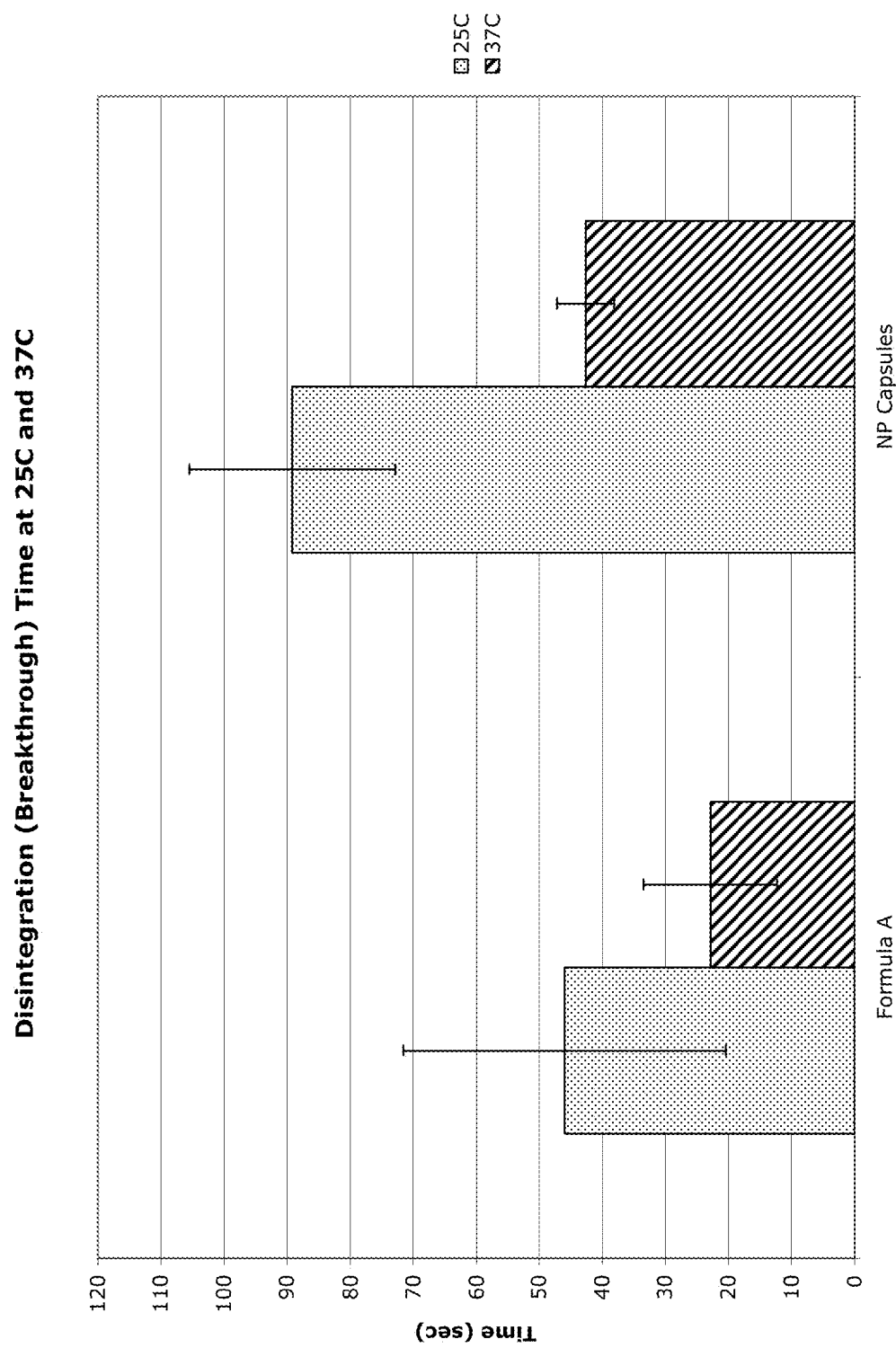
FIG. 2 shows average capsule disintegration times for Formula A capsules compared to commercial Capsugel NPcaps® capsules at 25° C. and 37° C.

In another aspect, the pullulan capsule exhibits rapid disintegration and dissolution in water. Such a capsule provides a platform for rapid mixing of the contents with water for ingestion via drinking or installation in body cavities. In one aspect, the hard capsule disintegrates in water at 37° C. in less than 25 seconds. Disintegration data for certain embodiments of the invention compared to commercial and conventional capsules at 37° C. is shown in FIG. 1. Disintegration time Formula A capsules compared to commercial Capsugel NPcaps® capsules at both 25° C. and 37° C. is shown in FIG. 2.

Figure 3:
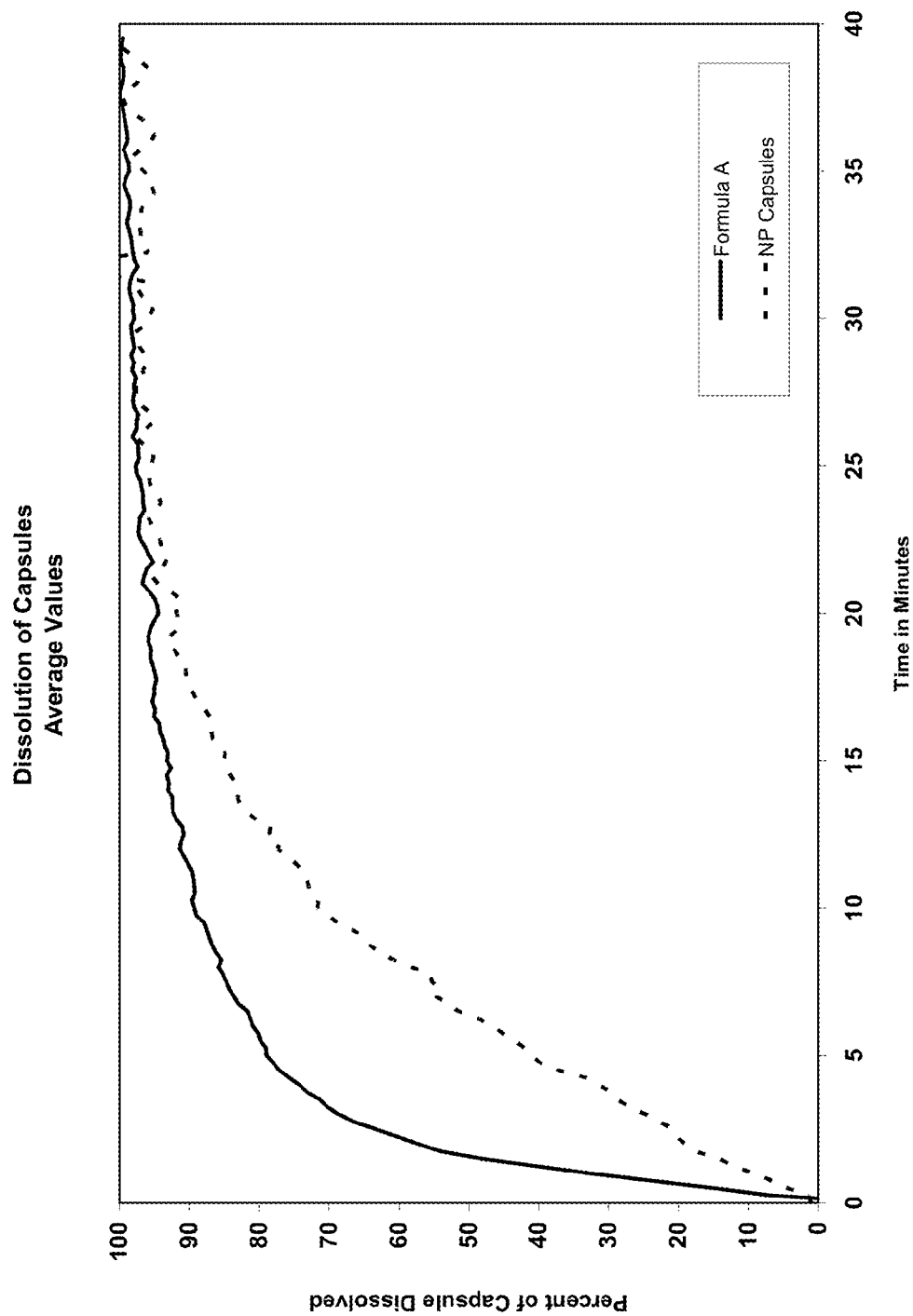
FIG. 3 shows average capsule dissolution profiles for Formula A capsules compared to commercial Capsugel NPcaps® capsules at 37° C.

In one aspect, 70% of the hard capsule dissolves in water at 37° C. in less than 5 minutes. Dissolution time for Formula A capsules compared to commercial Capsugel NPcaps® capsules at 37° C. is shown in FIG. 3.

In another aspect, the capsule further comprises an enteric coating for delivery to the gastrointestinal tract. In this aspect, the capsules are enteric coated for protection from the pH of the stomach and provide rapid delivery of the contents upon entering the small intestine. In one aspect, the container devices contain a pharmaceutical formulation and are used for the rapid oral, buccal, sublingual, gingival, pharyngeal, nasal, sinus, ophthalmic, rectal, or intravaginal administration of a pharmaceutical agent.

In another aspect, the capsule shell has a thickness between about 50 to 150 microns, 80 to 120 microns, 90 to 110 microns, and preferably 95 to 105 microns.

In one embodiment, the capsules are enteric coated for rapid delivery of one or more pharmaceutical agents in the small intestine. The enteric coating layer(s) may be applied onto the formulation comprising the pullulan using standard coating techniques. The enteric coating materials may be dissolved or dispersed in organic or aqueous solvents and may include one or more of the following materials: methacrylic acid copolymers (e.g. Eudragit), shellac, hydroxypropylmethcellulose phthalate, polyvinyl acetate phthalate, hydroxypropylmethylcellulose trimellitate, carboxymethylethylcellulose, cellulose acetate phthalate, cellulose triacetyl phthalate, sodium cellulose acetate phthalate, cellulose ester phthalate, cellulose ether phthalate, methylcellulose phthalate, cellulose ester-ether phthalate, hydroxy propyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, and polyvinyl acetate phthalate, or other suitable enteric coating polymer(s). The enteric materials are discussed in Remington's Pharmaceutical Sciences, which is periodically updated.

The pH at which the enteric coat will dissolve can be controlled by the polymer or combination of polymers selected and/or ratio of pendant groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates, or other plasticizers. Additives such as dispersants, colorants, anti-adhering, and anti-foaming agents may also be included. The enteric coating may be applied by press coating, molding, spraying, dipping, and/or air-suspension, or air tumbling procedures.

One method of applying the enteric coating is by pan coating, where the enteric coating is applied by spraying the enteric composition onto the capsules accompanied by tumbling in a rotating pan. Another method of applying the enteric coating is by fluidized bed coating. The enteric coating material may be applied to the capsules by employing solvents, including an organic, aqueous or a mixture of an organic and aqueous solvent. Exemplary solvents suitable in applying the enteric coating include an alcohol, ketone, ester, ether, aliphatic hydrocarbon, halogenated solvents, cycloaliphatic solvents, aromatic, heterocyclic, aqueous solvents, and mixtures thereof. In a preferred embodiment, the enteric coating consists of acrylic-based or poly(vinylacetate) phthalate based coating polymers in an aqueous dispersion. In preferred embodiments, the coating has a thickness from about 5 to 15% of the final dosage form.

The present disclosure further provides a rapidly dissolving film, the film comprising pullulan, one or more plasticizers, and one or more dissolution enhancing agents. The film is used to form receptacles, or envelopes, for the delivery of pharmaceutical agents. The film exhibits a normalized 100-micron film aqueous film breakthrough time of less than 20, 19, 18, 17, 16, 15, 14, 13, 12, 11, 10, 9, 8, or 7 seconds using the film breakthrough test described herein. In yet another aspect, the receptacle is a capsule which exhibits a normalized 100 micron film aqueous release time of less than 100, 95, 90, 85, 80, 75, 70, 65, 60, 55, or 50 seconds for complete release of DiPac® sugar as a test compound from the capsule using the test described herein. The contents preferably begin to release between about 7-20 seconds after placement of the receptacle into the oral cavity, nasal cavity, rectum, eye, or vagina of the patient.

The present disclosure further provides a pharmaceutical composition comprising a hard capsule shell, the capsule shell comprising pullulan, one or more plasticizers, and one or more dissolution enhancing agents; wherein the hard capsule shell is filled with a capsule fill formulation comprising one or more pharmaceutical agents and one or more excipients.

In one embodiment, the capsule shell comprises about 65 to 99 wt % pullulan, 0.1-10 wt % glycerin, 0.1-20 wt % polydextrose, 0-20 wt % maltose and 0-5 wt % of a sweetener. In another embodiment, the maltose is replaced by sorbitol. In another embodiment, the maltose is replaced by lactose. One specific embodiment provides capsule shells comprising 76 wt % pullulan, 7.6 wt % of glycerin, 7.6 wt % of polydextrose, 7.6% of maltose, and 0.8% of a sweetener as percent of total capsule shell solids. Another specific embodiment provides capsule shells comprising 71 wt % pullulan, 7 wt % glycerin, 7 wt % polydextrose, and 14 wt % sorbitol.

In one specific embodiment the disclosure provides a capsule shell formulation comprising about 70-80 wt % pullulan, about 5-10 wt % glycerol, about 5-10 wt % polydextrose, about 2-10 wt % maltose, about 1-5 wt % sorbitol, and about 1-5 wt % Solutol. In another aspect, sodium benzoate is included in the capsule shell formulations at about 0.05-0.5 wt % of the total dry weight of the formulation.

Capsule Fill Formulations

The capsule fill formulation comprises one or more pharmaceutical agents and one or more excipients. Exemplary pharmaceutical agents used in the capsule fill formulation are selected from one or more of, but not limited to:

cardioactive medications, including but not limited to organic nitrates such as nitroglycerin, isosorbide dinitrate and isosorbide mononitrates; quinidine sulfate; procainamide; thiazides such as bendroflumethiazide, chlorothiazide, and hydrochlorothiazide; nifedipine; nicardipine; adrenergic blocking agents, such as timolol, and propranolol; verapamil; diltiazem; captopril; clonidine; and prazosin and the like;

cardiovascular agents, including but are not limited to nitroglycerin, isosorbide dinitrate, captopril, enalapril, enalaprilat, quinapril, lisinopril, ramipril, losartan, amrinone, linnone, vesnerinone, hydralazine, nicorandil, prozasin, doxazosin, bunazosin, tarnulosin, yohimbine, propanolol, metoprolol, nadolol, atenolol, timolol, esmolol, pindolol, acebutolol, labetalol, phentolamine, cawedilol, bucindolol, verapamil, nifedipine, amlodipine, and dobutamine, or a sexual dysfunction agent like sildenafil citrate (Viagra);

diuretics, including but are not limited to acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, arniloride, triamterene, spironolactone, canrenone, and potassium canrenoate;

androgenic steroids, such as, testosterone; methyltestosterone, and fluoxymesterone, and the like;

estrogens, such as conjugated estrogens, esterified estrogens, estropipate, 17-betaestradiol, 17-beta-estradiol valerate, equilin, mestranol, estrone, estriol, 17-beta-ethinyl estradiol, and diethylstilbestrol, and the like;

progestational agents, such as progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-alphahydroxyprogesterone, dydrogesterone, dimethisterone, ethinylestrenol, norgestrel, demegestone, promegestone, and megestrol acetate, and the like;

central nervous system agents, for example sedatives, hyponotics, antianxiety agents, analgesics and anesthetics, such as buprenorphine, naloxone, haloperidol, fluphenazine, pentobarbital, phenobarbital, secobarbital, codeine, lidocaine, tetracaine, dyclonine, dibucaine, cocaine, procaine, mepivacaine, bupivacaine, etidocaine, prilocalne, benzocaine, fentanyl, and nicotine, and the like;

anesthetics, such as etomidate, ketamine, propofol, and benodiazepines (e.g., chlordiazepoxide, diazepame, clorezepate, halazepam, flurazeparn, quazepam, estazolam, triazolam, alprozolm, midazolam, temazepam, oxazepam, lorazepam), benzocaine, dyclonine, bupivacaine, etidocaine, lidocaine, mepivacaine, promoxine, prilocalne, procaine, proparcaine, ropivacaine, and tetracaine. Other useful agents may include amobarbital, aprobarbital, butabarbital, butalbital mephobarbital, methohexital, pentobarbital, phenobarbital, secobaxbital, thiopental, paral, chloralhydrate, ethchlorvynol, clutethimide, methyprylon, ethinamate, and meprobarnate;

psychotherapeutic agents, such as thorazine, serentil, mellaril, millazinetindal, permitil, prolixin, trilafon, stelazine, suprazine, taractan, navan, clozaril, haldol, halperon, loxitane, moban, orap, risperdal, alprazolam, chordiazepoxide, clonezepam, clorezepate, diazepam, halazepam, lorazepam, oxazepam, prazepam, buspirone, elavil, anatranil, adapin, sinequan, tofranil, surmontil, asendin, norpramin, pertofrane, ludiomil, pamelor, vivactil, prozac, luvox, paxil, zoloft, effexor, wellbutrin, serzone, desyrel, nardil, parnate, and eldepryl;

cancer chemotherapeutics agents, such as cisplatin (CDDP), procarbazine, mechlorethamine, cyclophosphamide, camptothecin, ifosfamide, melphalan, chlorambucil, bisulfan, nitrosurea, dactinomycin: dauno~ubicin, doxorubicin, bleomycin, plicomycin, mitomycin, etoposide (VP16), tamoxifen, taxol, transplatinum, 5-fluorouracil, vincristine, vinblastin, and methotrexate, or any analog or derivative variant thereof;

anti-inflammatory agents, such as hydrocortisone, cortisone, dexamethasone, fluocinolone, triamcinolone, medrysone, prednisolone, flurandrenolide, prednisone, halcinonide, methylprednisolone, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like;

antihistamines, such as diphenhydramine, dimenhydrinate, perphenazine, triprolidine, pyrilamine, chlorcyclizine, promethazine, carbinoxamine, tripelennamine, brompheniramine, hydroxyzine, cyclizine, meclizitle, clorprenaline, terfenadine, and chlorpheniramine, and the like. Other antihistamines are represented by, but are not limited to, cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prilamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine;

antacids, such as cimetidine, ranitidine, nizatidine, famotidine, omeprazole, bismuth antacids, metronidazole antacids, tetracycline antacids, clarithromycin antacids, hydroxides of aluminum, magnesium, sodium bicarbonates, calcium bicarbonate and other carbonates, silicates, and phosphates;

respiratory agents, such as theophilline and betaz-adrenergic agonists such as albuterol, terbutaline, metaproterenol, ritodrine, carbuterol, fenoterol, quinterenol, rimiterol, solmefamol, soterenol, tretoquinol, and the like;

sympatholnimetics such as dopamine, norepinephrine, phenylpropanolamine, phenylephrine, pseudoephedrine, amphetamine, propylhexedrine, epinephrine, and the like;

miotics, such as pilocarpine, and the like; Cholinergic agonists, such as choline, acetylcholine, methacholine, carbachol, bethanechol, pilocarpine, muscarine, and arecoline, and the like;

antimuscarinic or muscarinic cholinergic blocking agents, such as atropine, scopolamine, homatropine, methscopolamine, homatropine methylbromide, methantheline, cyclopentolate, tropicamide, propantheline, anisotropine, dicyclomine, eucatropine, and the like;

mydriatics, such as atropine, cyclopentolate, homatropine, scopolamine, tropicamide, eucatropine, hydroxyamphetamine, and the like. Anti-infectives, such as antibiotics, including penicillin, tetracycline, chloramphenicol, sulfacetamide, sulfamethazine, sulfadiazine, sulfamerazine, sulfamethizole and sulfisoxazole; antivirals, including idoxuridine; antibacterials, such as erythromycin and clarithrwmycin; and other anti-infectives including nitrofurazone, and the like. Antifungal agents that may be delivered include but are not limited to ketoconazole, fluconazole, nystatin, itraconazole, clomitrazole, and amphotericin B. Antiviral agents that may be used include but are not limited to acyclovir, trifluridine, idoxomdine, foscarnet, ganciclovir, zidovudine, dideoxycytosine, dideoxyinosine, stavudine, famciclovir, didanosine, zalcitabine, rifimantadine, and cytokines;

antimicrobial agents, such as naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, Plactamase inhibitors; meziocillin, piperacillin, aztreonam, norfloxacin, trimethoprim, ceftazidime, and dapsone;

humoral agents, such as the prostaglandins, natural and synthetic, for example PGEI, PGE 2-alpha, and PGF 2-alpha, the PGEI analog misoprostol, and the like;

antispasmodics, such as atropine, methantheline, papaverine, cinnamedrine, methscopolamine, and the like;

antidepressant drugs, such as isocarboxazid, phenelzine, tranylcyprornine, imipramine, amitriptyline, trimipramine, doxepin, desipramine, nortriptyline, protriptyline, amoxapine, maprotiline, trazodone, and the like;

anti-diabetics, such as insulin and metformin;

anorectic drugs, such as, dextroamphetamine, methamphetamine, phenylpropanolamine, fenfluramine, diethylpropion, mazindol, phentennine, and the like;

decongestants and antitussives include agents such as dextromethorphan hydrobromide, levopropoxyphene napsylate, noscapine, carbctapentane, caramiphen, chlophedianol, pseudoephedrine hydrochloride, pseudoephedrine sulfate, phenylephidrine, diphenhydramine, glaucine, pholcodine, and benzonatate;

anti-allergenics, such as antazoline, methapyrilene, chlorpheniramine, pyrilamine, pheniramine, and the like;

tranquilizers, such as reserpine, chlorpromazine, and anti-anxiety benzodiazepines such as alprazolam, chlordiazepoxide, clorazeptate, halazepam, oxazepam, prazepam, clonazepam, flurazepam, triazolam, lorazepam, diazepam, and the like;

antipsychotics, such as thiopropazate, chlorpromazine, triflupromazine, mesoridazine, piperacetazine, thioridazine, acetophenazine, fluphenazine, perphenazine, trifluoperazine, chlorprothixene, thiothixene, haloperidol, bromperidol, loxapine, molindone, and the like;

decongestants, such as phenylephrine, ephedrine, naphazoline, tetrahydrozoline, and the like;

antipyretics, such as aspirin, salicylamide, and the like;

anti-migraine agents, such as dihydroergotamine, pizotyline, and the like;

drugs for treating nausea and vomiting, such as chlorpromazine, perphenazine, prochlorperazine, promethazine, triethylperazine, triflupromazine, and trirneprazine, ondansetron, granisetron, tropisetron, azasetron, dolasteron and the like;

anti-malarials, such as the 4-aminoquinolines, alphaminoquinolines, chloroquine, pyrimcthamine, and the like;

anti-ulcerative agents, such as misoprostol, omeprazole, enprostil, and the like;

peptides, such as growth releasing factor and the like. Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like;

analgesics include opioids and other medicaments such as morphine, mepidine, dentanyl, sufentranil, alfentanil, aspirin, acetaminophen, ibuprofen, indomethacine, naproxen, isocome, midrin, axotal, firinal, phrenilin, ergot, and ergot derivatives (wigraine, cafergot, ergostat, ergomar, dihydroergotamine), imitrex, and ketoprofen; and anti-estrogen or hormone agents, such as tamoxifen or human chorionic gonadotropin, and the like.

The pharmaceutical can be in its free-base or acid form, or in the form of salts, esters, or any other pharmacologically acceptable derivatives, enantomerically pure forms, tautomers as components of molecular complexes. The amount of drug to be incorporated in the composition varies depending on the particular drug, the desired therapeutic effect, and the time span for which the device is to provide therapy. The pharmaceutical may be formulated using various excipients, disintegrants, lubricants, fillers, flow aids, taste masking agents, absorption enhancing agents, surfactants, flavors, salivary stimulants and other formulation agents known to those skilled in the art.

In one aspect, the pharmaceutical agent is a vitamin, cofactor, or dietary supplement.

The capsule fill formulation may further contain one or more excipients. In one aspect, the excipient is a hydrophilic excipient such as a water soluble polymer or sugar that can serve as a bulking agent or as a wetting agent such as surfactant, a sugar, and/or a tonicity agent. Upon contact with an aqueous medium, water penetrates through the disintegrating capsule to dissolve the water soluble excipients in the capsule fill. Further optional excipients include one or more of disintegrants, flow agents, lubricants and film coating for taste masking One of skill in the art can select appropriate excipients for use in the drug compositions for capsule fill, considering a variety of factors, such as the drug to be administered, the route of administration, the dosage, and the preferred dissolution rate. For example, the excipients can function as bulking agents, release-modifiers, wetting agents, tonicity agents, or combinations thereof. Preferred excipients include hydrophilic polymers, wetting agents, and sugars. The amount of excipient in the drug matrix is less than about 95%, more preferably less than about 80%, by weight of the capsule fill.

In one embodiment, hydrophilic polymers can be used in the drug compositions described herein. Hydrophilic polymers include both synthetic and natural polymers, either non-biodegradable or biodegradable. Representative synthetic polymers include polyethylene glycol ("PEG"), polyvinyl pyrrolidone, polymethacrylates, polylysine, poloxamers, polyvinyl alcohol, polyacrylic acid, polyethylene oxide, and polyethyoxazoline. Representative natural polymers include albumin, alginate, gelatin, acacia, chitosan, cellulose dextran, ficoll, starch, hydroxyethyl cellulose, hydroxypropyl cellulose, hydroxy-propylmethyl cellulose, hyaluronic acid, carboxyethyl cellulose, carboxymethyl cellulose, deacetylated chitosan, dextran sulfate, and derivatives thereof. Preferred hydrophilic polymers include PEG, polyvinyl pyrrolidone, poloxamers, hydroxypropyl cellulose, and hydroxyethyl cellulose.

The hydrophilic polymer selected for use in a particular capsule fill drug composition is based on a variety of factors, such as the polymer molecular weight, polymer hydrophilicity, and polymer inherent viscosity. The hydrophilic polymer can be used as a bulking agent or as a wetting agent.

Representative sugars that can be used in the capsule fill drug compositions include mannitol, sorbitol, xylitol, glucitol, ducitol, inositiol, arabinitol; arabitol, galactitol, iditol, allitol, fructose, sorbose, glucose, xylose, trehalose, al lose, dextrose, altrose, gulose, idose, galactose, talose, ribose, arabinose, xylose, lyxose, sucrose, maltose, lactose, lactulose, fucose, rhamnose, melezitose, maltotriose, and raffinose. Preferred sugars include mannitol, lactose, sucrose, sorbitol, trehalose, glucose, and are adjusted to provide osmolality or to provide wetting of the porous drug matrix or the drug microparticles within the matrix.

Wetting agents can be used in the capsule fill drug composition to facilitate water ingress into the disintegrating capsule and wetting of the drug or drug particles in order to facilitate dissolution. Representative examples of wetting agents include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethlylene castor oil derivatives, polyoxyethylene sorbitan fatty acid esters (e.g., TWEEN™s), polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthlate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type, also known as superinone or triton) is another useful wetting agent. Most of these wetting agents are known pharmaceutical excipients and are described in detail in the Handbook of Pharmaceutical Excipients, published jointly by the American Pharmaceutical Association and The Pharmaceutical Society of Great Britain (The Pharmaceutical Press, 1986).

Preferred wetting agents include polyvinylpyrrolidone, polyethylene glycol, tyloxapol, poloxamers such as PLURONIC™F68, F127, and F108, that are block copolymers of ethylene oxide and propylene oxide, and polyxamines such as TETRONIC™908 (also known as POLOXAMINE™908), that is a tetrafunctional block copolymer derived from sequential addition of propylene oxide and ethylene oxide to ethylenediamine (available from BASF), dextran, lecithin, dialkylesters of sodium sulfosuccinic acid such as AEROSOL™OT, that is a dioctyl ester of sodium sulfosuccinic acid (available from American Cyanamid), DUPONOL™P, that is a sodium lauryl sulfate (available from DuPont), TRITON™X-200, that is an alkyl aryl polyether sulfonate (available from Rohm and Haas), TWEEN™20 and TWEEN™80, that are polyoxyethylene sorbitan fatty acid esters (available from ICI Specialty Chemicals), Carbowax 3550 and 934, that are polyethylene glycols (available from Union Carbide), Crodesta F-110, that is a mixture of sucrose stearate and sucrose distearate, and Crodesta SL-40 (both available from Croda Inc.), and SA90HCO, that is $C_{18}H_{37}CH_2$ (CON(CH$_3$)CH$_2$ (CHOH)$_4$ CH$_2$ OH)$_2$.

Wetting agents which are particularly useful include Tetronic 908, the Tweens, Pluronic F-68 and polyvinylpyrrolidone. Other useful wetting agents include decanoyl-N-methylglucamide; n-decyl-β-D-glucopyranoside; n-decyl-β-D-maltopyranoside; n-dodecyl-β-D-glucopyranoside; n-dodecyl-β-D-maltoside; heptanoyl-N-methylglucamide; n-heptyl-β-D-glucopyranoside; n-heptyl-β-D-thioglucoside; n-hexyl-β-D-glucopyranoside; nonanoyl-N-methylglucamide; n-octyl-β-D-glucopyranoside; octanoyl-N-methylglucamide; n-octyl-β-D-glucopyranoside; and octyl-β-D-thioglucopyranoside. Another preferred wetting agent is p-isononylphenoxypoly(glycidol), also known as Olin-10G or Surfactant 10-G (commercially available as 10G from Olin Chemicals). Two or more wetting agents can be used in combination.

The capsule fill drug composition may include one or more tonicity agents, such as salts (e.g., as sodium chloride or potassium chloride) or sugars (such as mannitol, dextrose, sucrose, or trehalose) to adjust a hypotonic solution of a drug to isotonic so that the drug, when in solution, is physiologically compatible with the cells of the body tissue of the patient. The type and amount of tonicity agent can be selected by one of skill in the art using known techniques.

In one aspect, the capsule fill formulation optionally further comprises one or more sweeteners. The sweetener is generally present in the encapsulated product from about 0.1% to about 70% by weight of the final encapsulated product. The sweetener is selected from one or more of the sweeteners presented above. The present inventive subject matter also contemplates having a blend of sweeteners as the active ingredient in the encapsulated product.

In one aspect, the capsule fill formulation optionally further comprises one or more flavoring agents. The flavoring is optionally present in the encapsulated product from about 0.1% to about 5% by weight of the final encapsulated product. The flavoring agents selected from one or more of the sweeteners presented above.

In one aspect, the capsule fill formulation optionally further comprises one or more disintegrants. Disintegrants include compounds used in solid dosage forms to promote the disruption of the solid mass into smaller particles that are more readily dispersed or dissolved. Exemplary disintegrants include, by way of example and without limitation, starches such as corn starch, potato starch, pre-gelatinized and modified starches thereof, sweeteners, clays such as bentonite, microcrystalline cellulose (e.g., Avicel), methyl cellulose, carboxymethylcellulose calcium, sodium carboxymethylcellulose, hydroxy propylcellulose-low substituted, colloidal silicon dioxide, alginic acid, sodium alginate, cellulose polyacrilin potassium (e.g., Amberlite), alginates, sodium starch glycolate, gums, agar, guar, locust bean, karaya, xanthan, pectin, tragacanth, agar, bentonite, polyvinylpyrrolidone and other materials known in the art.

In one aspect, the capsule fill formulation optionally further comprises one or more flow agents, or glidants. Glidants are agents used in solid dosage formulations to promote flowability of the solid mass. Such compounds include, by way of example and without limitation, colloidal silica, cornstarch, talc, calcium silicate, magnesium silicate, colloidal silicon, tribasic calcium phosphate, silicon hydrogel and other materials known in the art.

It is contemplated that the capsule fill may optionally comprise compressed tablets, beads, microparticulates, foaming agents and/or granules. In one aspect, the capsule fill formulation optionally further comprises one or more lubricants. Lubricants include substances used in solid dosage formulations to reduce friction during compression. Such compounds include, by way of example and without limitation, sodium oleate, sodium stearate, calcium stearate, zinc stearate, magnesium stearate, polyethylene glycol, talc, mineral oil, stearic acid, sodium benzoate, sodium acetate, sodium chloride, and other materials known in the art.

In one aspect, the capsule fill formulation further comprises an optional foaming agent. The foaming agent is selected from one or more of the group consisting of polyethylene glycol, saponin, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate and lauromacrogol.

In one aspect, the optional capsule fill comprising compressed tablets, beads, microparticulates, and/or granules may further comprise a film coating for taste masking of the capsule fill. For example, the coating may be prepared from a commercially available powder mix such as OPADRY® which is available from Colorcon, that typically comprises hypromellose, polyethylene glycol, polysorbate, and colorants, e.g. titanium dioxide and iron oxide. Further films employed for taste masking include the Eudragits and ethylcellulose based films.

EXAMPLES

Example 1

Preparation of Pullulan Films

In this example, pullulan films containing a wide variety of generally accepted as safe ("GRAS") ingredients were prepared. The physical properties and film breakthrough time of the films were measured.

Films were prepared by dissolving the added ingredient(s) in water followed by suspending pullulan powder in the water and warming the suspension until the pullulan was dissolved. The pullulan used in all experiments was pullulan PI-20 with a reported molecular weight of 200 K Daltons obtained from Hayashibara Co., LTD. This procedure was carried out in a 250 mL beaker using a stir bar for mixing. The beaker was mixed on a non-heater stir plate and then transferred to a heated stir plate. The solution was poured into a 50 mL conical polypropylene centrifuge tube and centrifuged at 3000 to 4000 rpm in a Fisher Scientific Marathon Centrifuge for about one minute to speed removal of any bubbles present. The clear solution was poured onto a plate glass and a knife edge pulled over it set at a distance of 1 mm above the plate. The films were allowed to dry at room temperature. After drying, the films were removed from the plate, the flexibility, clarity, film thickness, and "film breakthrough" time determined.

The examples all use 3 gm of pullulan and 20 gm of water and 3 or 0.3 gm of the added ingredient.

Flexibility was determined by folding a small portion of the film back on itself several times. The film was judged flexible if it did not break. It was listed as brittle if it broke.

The film thickness was determined at several places on the film used to run the film breakthrough tests using a Digimatic caliper from Mitutoyo.

The film breakthrough time was determined from the time required for a 1 gram tablet to fall through the film when placed in 37° C. water using an apparatus and technique described below.

A two-inch square section of the film was used in the measurement which was clamped in the apparatus, a small hole punched in the film to allow air to exit, the tablet placed on top, the apparatus lowered into the water and the time between immersion of the film and when the tablet falls through the film was measured. Because all the films are not of the same thickness, a correction was made on the film breakthrough time numbers by normalizing the time for a 100-micron thick film. The ingredients investigated include polyvinyl alcohol (PVA 85-38), polydextrose, maltose, gluconic acid lactone, guar gum, glycerin, albumin, sodium starch glycolate, sorbitol, and Pluronic F-127. The normalized film breakthough times were compared to that, of a pullulan film with no added ingredients. Ingredients that decreased the normalized film breakthrough time relative to pullulan alone are summarized in Table 1.

TABLE 1

Effect of Added Ingredients on Pullulan Film Breakthrough Time.

| Added Ingredient | Amount Added (Percent of Pullulan weight) | Film Thickness (microns) | Normalized Film Breakthrough time (Sec/100 μm Film) |
| --- | --- | --- | --- |
| None | 10 | 80 | 18.95 |
| PVA (85-38) | 10 | 100 | 12.64 |
| Polydextrose | 10 | 75 | 18.76 |
| Maltose | 10 | 110 | 15.55 |
| Gluconic Acid Lactone | 10 | 70 | 16.54 |
| Guar Gum | 10 | 100 | 17.97 |
| Glycerin | 10 | 70 | 15.38 |
| Albumin | 10 | 65 | 18.06 |
| Sodium Starch Glycolate | 10 | 95 | 16.47 |
| Sorbitol | 10 | 90 | 16.53 |
| Pluronic F-127 | 10 | 70 | 16.10 |

Example 2

Variation of Added Ingredient Amount

The ten films with the most rapid film breakthrough times in Table 1 were further studied at a higher concentration of the respective added ingredient. The first study was at 10% by weight of the pullulan amount and the second study was performed using 20% by weight of the pullulan amount. The water was 20 gm and the pullulan was 3 gm in all experiments. The film breakthrough times are normalized for a 100-micron thick film. The results are summarized in Table 2, below. The data from Table 1 are included for reference.

TABLE 2

Variation of Added Ingredient Amount and Effect on Breakthrough Time.

| Added Ingredient | Amount Added (Percent of Pullulan weight) | Film Thickness (microns) | Normalized Film Breakthrough time (Sec/100 μm Film) |
| --- | --- | --- | --- |
| None | — | 80 | 18.95 |
| PVA (85-38) | 10 | 100 | 12.64 |
| PVA (85-38) | 20 | 85 | 16.0 |
| Polydextrose | 10 | 75 | 18.76 |
| Polydextrose | 20 | 70 | 19.8 |
| Maltose | 10 | 110 | 15.55 |
| Maltose | 20 | 70 | 17.0 |
| Gluconic Acid Lactone | 10 | 70 | 16.54 |
| Gluconic Acid Lactone | 20 | 100 | 18.1 |
| Guar Gum | 10 | 100 | 17.97 |
| Guar Gum | 20 | 100 | 22.8 |
| Glycerin | 10 | 70 | 15.38 |
| Glycerin | 20 | 170 | 16.0 |
| Albumin | 10 | 65 | 18.06 |
| Albumin | 20 | 100 | 7.7 |
| Sodium Starch Glycolate | 10 | 95 | 16.47 |
| Sodium Starch Glycolate | 20 | 100 | 19.5 |
| Sorbitol | 10 | 90 | 16.53 |
| Sorbitol | 20 | 75 | 7.5 |
| Pluronic F-127 | 10 | 70 | 16.10 |
| Pluronic F-127 | 20 | 60 | 12.2 |

The clarity of the film was determined as clear, translucent or opaque. Clear—objects behind film clearly discernable; translucent—objects behind film not discernable except right next to the film; and opaque—very poor light transmission.

Observations of the films were as follows. Increased PVA resulted in a translucent film, with good strength and flexibility. Increased polydextrose resulted in a translucent film but the film was brittle. Increased maltose resulted in a similar film, but the film was thinner and more brittle. Increased gluconic acid lactone resulted in similar films, but the films were brittle and thicker with increasing concentration. Increasing guar gum resulted in a translucent film but the film was not smooth. Increased glycerin resulted in a much thicker film with a similar normalized film breakthrough time. Increased albumin caused the film to stick to glass. Increased sodium starch glycolate resulted in a translucent film but the film was not smooth. The higher amount of sorbitol resulted in a clear film that was smooth on both sides with a faster normalized film breakthrough time. Increased pluronic F-127 resulted in a film that was translucent with a smooth waxy feeling.

For a clear, flexible, and smooth film, PVA, polydextrose, glycerin, maltose, gluconic acid lactone, and sorbitol are preferable. For a rough translucent film, guar gum, albumin, sodium starch glycolate, and pluronic F-127 are preferable.

Example 3

Mixtures of Added Ingredients

In this study the following added ingredients were paired to determine the properties of the resulting films at 10% by weight each of the pullulan amount: (1) PVA and glycerin; (2) PVA and sorbitol; (3) PVA and polydextrose; (4) PVA and maltose; (5) PVA and gluconic acid lactone; (6) polydextrose and glycerin; (7) polydextrose and maltose; (8) polydextrose and gluconic acid lactone; (9) polydextrose and sorbitol; (10) maltose and glycerin; (11) gluconic acid lactone and glycerin; (12) sorbitol and glycerin; (13) gluconic acid lactone and sorbitol; (14) maltose and sorbitol; and (15) maltose and gluconic acid lactone. The water was 20 gm and the pullulan was 3 gm in all experiments. The film breakthrough times are normalized for a 100-micron thick film. The results are summarized in Table 3.

The films with the most rapid breakthrough times contain maltose and polydextrose, glycerin and maltose, or glycerin and polydextrose.

Example 4

Films Containing Pullulan and Combinations of Glycerin, Maltose, and Polydextrose The purpose of this example was to incorporate variations of three added ingredients giving the most rapid film breakthrough times in prior examples. In this study the amounts of glycerin, polydextrose and maltose were varied from 10 to 20% by weight of the pullulan amount. The film breakthrough times are normalized for a 100-micron thick film. The results are summarized in Table 4.

TABLE 3

Effect of Added Ingredient Combinations on Film Breakthrough Time.

| Added Ingredient | Amount Added (Percent of Pullulan weight) | Film Thickness (microns) | Normalized Film Breakthrough time (Sec/100 μm Film) | Comments |
|---|---|---|---|---|
| PVA | 10 | 70 | 15.3 | Slightly Opaque |
| Glycerin | 10 | | | Strong, Flexible |
| PVA | 10 | 70 | 14.0 | Slightly Opaque |
| Sorbitol | 10 | | | Strong, Flexible |
| PVA | 10 | 70 | 16.0 | Slightly Opaque |
| Polydextrose | 10 | | | Strong, Flexible |
| PVA | 10 | 70 | 15.7 | Clear |
| Maltose | 10 | | | Strong, Flexible |
| PVA | 10 | 70 | 19.7 | Clear |
| Gluconic Acid Lactone | 10 | | | Strong, Flexible |
| Polydextrose | 10 | 70 | 11.7 | Clear |
| Glycerin | 10 | | | Strong, Brittle |
| Polydextrose | 10 | 70 | 10.7 | Clear |
| Maltose | 10 | | | Strong, Brittle |
| Polydextrose | 10 | 80 | 15.8 | Clear |
| Gluconic Acid Lactone | 10 | | | Strong, Brittle |
| Polydextrose | 10 | 75 | 15.6 | Clear |
| Sorbitol | 10 | | | Strong, Brittle |
| Maltose | 10 | 65 | 11.2 | Clear |
| Glycerin | 10 | | | Strong, Flexible |
| Gluconic Acid Lactone | 10 | 50 | 12.1 | Clear Strong, Flexible |
| Glycerin Sorbitol | 10 | NA | — | Clear Strong, Brittle |
| Glycerin | 10 | | | |
| Gluconic Acid Lactose Sorbitol | 10 | 70 | 12.4 | Clear Strong, Flexible |
| Maltose | 10 | 70 | 13.7 | Clear |
| Sorbitol | 10 | | | Strong, Brittle |
| Maltose | 10 | 100 | 15.5 | Clear |
| Gluconic Acid Lactone | 10 | | | Strong, Brittle |

TABLE 4

Effect of Combination of Formulations on Film Breakthrough Time.

| Film Number | Ingredients | Amount of material (g) | Film Thickness (μm) | Normalized Film Breakthrough Time (sec) |
|---|---|---|---|---|
| 1 | Water | 20 | 90 | 10.8 |
|   | Pullulan | 3 | | |
|   | Glycerin | 0.3 | | |
|   | Polydextrose | 0.3 | | |
|   | Maltose | 0.3 | | |
| 2 | Water | 20 | 120 | 10.0 |
|   | Pullulan | 3 | | |
|   | Glycerin | 0.6 | | |
|   | Polydextrose | 0.3 | | |
|   | Maltose | 0.3 | | |
| 3 | Water | 20 | 120 | 14.0 |
|   | Pullulan | 3 | | |
|   | Glycerin | 0.3 | | |
|   | Polydextrose | 0.6 | | |
|   | Maltose | 0.3 | | |
| 4 | Water | 20 | 110 | 10.7 |
|   | Pullulan | 3 | | |
|   | Glycerin | 0.3 | | |
|   | Polydextrose | 0.3 | | |
|   | Maltose | 0.6 | | |
| 5 | Water | 20 | 110 | 8.0 |
|   | Pullulan | 3 | | |
|   | Glycerin | 0.6 | | |
|   | Polydextrose | 0.6 | | |
|   | Maltose | 0.3 | | |
| 6 | Water | 20 | 110 | 6.5 |
|   | Pullulan | 3 | | |
|   | Glycerin | 0.6 | | |
|   | Polydextrose | 0.3 | | |
|   | Maltose | 0.6 | | |
| 7 | Water | 20 | 90 | 8.9 |
|   | Pullulan | 3 | | |
|   | Glycerin | 0.3 | | |
|   | Polydextrose | 0.6 | | |
|   | Maltose | 0.6 | | |
| 8 | Water | 20 | 120 | 10.4 |
|   | Pullulan | 3 | | |
|   | Glycerin | 0.6 | | |
|   | Polydextrose | 0.6 | | |
|   | Maltose | 0.6 | | |

Of the films in Table 4, the ones determined to have the best properties (strong, flexible and not brittle) were film Nos. 1, 3, 4, and 7.

Example 5

Films Containing Pullulan and Varied Amounts of Glycerin, Maltose, and Polydextrose This example varied the amount of glycerin, polydextrose, and maltose from 10 to 15% of the pullulan amount and compared the properties of the films. The film breakthrough times are normalized for a 100-micron thick film. The results are summarized in Table 5.

TABLE 5

Effect of Varied Added Ingredients Amount on Film Breakthrough Time.

| Film Number | Ingredients | Amount of material (g) | Film Thickness (μm) | Film Breakthrough Time (sec) | Normalized Film Breakthrough Time (sec) |
|---|---|---|---|---|---|
| 1 | Water | 20 | 105 | 14.3 | 13.6 |
|   | Pullulan | 3 | | | |
|   | Glycerin | 0.3 | | | |
|   | Polydextrose | 0.3 | | | |
|   | Maltose | 0.3 | | | |
| 2 | Water | 20 | 120 | 15.6 | 13.0 |
|   | Pullulan | 3 | | | |
|   | Glycerin | 0.45 | | | |
|   | Polydextrose | 0.3 | | | |
|   | Maltose | 0.3 | | | |
| 3 | Water | 20 | 80 | 8.4 | 10.5 |
|   | Pullulan | 3 | | | |
|   | Glycerin | 0.3 | | | |
|   | Polydextrose | 0.45 | | | |
|   | Maltose | 0.3 | | | |
| 4 | Water | 20 | 90 | 9.6 | 10.7 |
|   | Pullulan | 3 | | | |
|   | Glycerin | 0.3 | | | |
|   | Polydextrose | 0.3 | | | |
|   | Maltose | 0.45 | | | |

All of the films had rapid film breakthrough times and acceptable properties.

Example 6

Preparation of Pullulan Capsules

In this example, prototype capsules were prepared using pin bars as the molds for the capsule shells. Stainless steel pins were machined to a diameter of 7.50 mm (0.295 inches) for the capsule body and 7.55 mm (0.297 inches) for the capsule cap. The pill bars were polished to a very reflective surface. These pin bars are close to the size of a standard number 0 capsule.

The formulation for preparing the capsule bodies and caps is set forth in Table 6.

TABLE 6

Formulation of Capsules.

| | |
|---|---|
| Water | 20 g |
| Pullulan | 8 g |
| Glycerin | 0.8 g |
| Polydextrose | 0.8 g |
| Maltose | 0.8 g |

The procedure used to prepare the solution for capsule manufacture is as follows. The glycerin, polydextrose, and maltose were dissolved in the water in a beaker employing a stirring plate and stir bar. The pullulan was added, stirred with a spatula to suspend the pullulan in water. The suspension was heated until the pullulan dissolved and the temperature was above 60° C. The solution was poured into a plastic 50-mL conical centrifuge tube and centrifuged at more than about 3,000 rpm to speed the removal of any bubbles present. The centrifuge tube was placed in a water bath and heated to about 65° C. The pin bars were then dipped into the solution, removed and excess solution was allowed to drain. The pin bars were then placed upright on a plate and allowed to dry. The capsule films were cut around the pin bars longer than the final length and the excess removed from the pin bars. The capsule body or caps were then pushed off the pins using a Teflon washer that was split so that it could be expanded and tightened around the pin bar.

The capsule body and caps were cut to length (similar to a number 0 capsule) and the body and cap joined together to form the final capsule. The results from several batches yielded capsules with a film thickness ranging from 60 to 120 microns.

Because the capsules are designed to dissolve in the oral cavity, it was thought desirable to provide a pleasant sweet taste to the capsule shells. A batch of capsules was prepared by incorporating an artificial sweetener, acesulfame K (an intense sweetener for use in pharmaceuticals). The formulation is described in Table 7.

TABLE 7

Formulation of Capsules with Sweetener.

| | |
|---|---|
| Water | 26.7 g |
| Pullulan | 12 g |
| Glycerin | 1.2 g |
| Polydextrose | 1.2 g |
| Maltose | 1.2 g |
| Acesulfame | 0.12 g |

The capsule shells were prepared as described above. The capsules were filled with DiPac® Direct compacting and tableting sugar and the time for the release of the sugar from the capsule was determine in 37° C. water with no stirring. The capsules all released the majority of their contents in less than one minute, normally between 20 and 50 seconds.

Example 7

Comparison to Pullulan Formulations of Prior Art

This example compared the film breakthrough time of capsules prepared according to Example 16 of U.S. Pat. No. 3,784,390 (1-Iayashibara Biochemical Laboratories, Incorporated, Okayama-ken, Japan) with those prepared in accordance with the present invention.

Example 16 of the '390 patent recites that a solution comprised of three parts of a 7% solution of pullulan A (mean molecular weight of 250,000) was mixed with one part of a solution of gelatin at 70° C. Thus, this corresponds to a solution comprising three parts of a solution of 7 g pullulan per 100 gm water plus one part of a solution of 20 gm gelatin per 100 g water.

Attempts to prepare capsules of the material specified in the first paragraph of Example 16 of the '390 patent were not successful because the solution was not sufficiently viscous to adhere to the pins. Several attempts were made to blow heated air on the material on the pins and also to cool the pins and blow the surface to evaporate the water with no success. Additionally, attempts to cast films with this formulation failed as the samples were heterogeneous and contained gaps and lacked integrity.

A second part of Example 16 of the '390 patent used equal amounts of a pullulan and a gelatin solution and 1% maltitol. No concentration of the materials used was given. However, assuming the concentration was the same as the first part of the example, this corresponds to a solution comprising 4 gm pullulan, 4 gm gelatin, 0.08 gm maltitol and 30 gm water.

Attempts to prepare capsules of the material specified in the second paragraph of Example 16 of the '390 patent were not successful because the solution was not sufficiently viscous to adhere to the pins. Several attempts were made to blow heated air on the material on the pins and also to cool the pins and blow the surface to evaporate the water with no success.

Attempts to cast films with this formulation were also unsuccessful. Further additional solutions were prepared containing lower amounts of water according to Formulations 1 and 2 in Table 8. Since the type of gelatin was not specified, both acid and base washed gelatin were investigated.

TABLE 8

Composition of Test Formulations.*

| | Modified Example 16 of '390 Patent (first paragraph) | Modified Example 16 of '390 Patent (second paragraph) | Formulation 1 | Formulation 2 | Formulation 3 | Formulation 4 |
|---|---|---|---|---|---|---|
| Water | 200 g or 30 g | 200 g or 30 g | 30 g | 30 g | 30 g | 30 g |
| Pullulan | 21 g or 3.15 g | 7 g or 1.06 g | 4 g | 4 g | 4 g | 4 g |
| Gelatin | 20 g or 3.0 g | 20 g or 3.0 g | 4 g (Gelatin A) | 4 g (Gelatin B) | 4 g (Gelatin A) | 4 g (Gelatin B) |
| Maltitol | None | 1 wt % or 0.3 g | 0.16 g | 0.16 g | 0.8 g | 0.8 g |

*Gelatin A is acid washed; gelatin B is base washed.

In addition, a formulation of the present invention, Formula A, was prepared according to the formula in Table 9.

TABLE 9

Formula A Capsule Formulation.

| | |
|---|---|
| Water | 26.7 g |
| Pullulan | 12.0 g |
| Glycerin | 1.2 g |
| Polydextrose | 1.2 g |
| Maltose | 1.2 g |
| Acesulfame | 0.12 g |

It is understood that the Formula A capsule formulation is scalable, as shown in Example 12.

To prepare Formulations 1, 2, 3, and 4 in Table 8, the maltitol was dissolved in the water and the pullulan dispersed and dissolved in the maltitol solution at 70° C. The gelatin was then added and dissolved in the resulting solution that was centrifuged to remove any bubbles in the sample. In contrast to formulations from Example 16 of the '390 patent, these formulations were sufficiently viscous to stick on the capsule pins at about 70° C. However, the pins had to be dipped several times to achieve a target capsule film thickness of approximately 100 microns upon drying. Capsules of Formulations 1 through 4 were opaque, rough, and brittle with multiple fine cracks. Additionally, cast films of Formulations 3 and 4 were also produced, although the films were opaque and brittle. Attempts to produce cast films from formulations 1 and 2 of Table 8 were unsuccessful.

To prepare the Formula A capsule formulation according to Table 9, all the ingredients except the pullulan were dissolved in the water. The pullulan was then dispersed in this solution and the solution was heated to about 65° C. to dissolve the pullulan. The material was centrifuged to speed removal of any bubbles in the sample. The formulation was sufficiently viscous at 65 to 70° C. to provide a layer of material on the pins that produces a capsule film thickness of approximately 100 microns after drying. Capsules of the present invention were clear and flexible, as was a cast film produced from the formulation of the present invention.

Example 8

Film Breakthrough of Films

The film breakthrough study was performed using the same procedure as described previously using the film breakthrough apparatus described and shown herein. The film breakthrough times were normalized to that of a 100-micron film and the test was repeated four times for each film. The results are summarized in Table 10.

TABLE 10

Film Breakthrough times of Comparative Films.

| Formulation | Average Film Thickness (microns) | Normalized Film Breakthrough Time (Sec; n = 4) |
|---|---|---|
| Table 8; #3 | 125 | 51.4 ± 22.0 |
| Table 8; #4 | 135 | 61.5 ± 6.6 |
| Formula A | 125 | 11.3 ± 4.9 |

Example 9

Preliminary Content Release Times of Pullulan Capsules

The test capsules were filled with DiPac® Direct Compacting and Tableting.

Formulation Sugar (Domino Specialty Ingredients). The release testing was performed in a USP dissolution flask filled with water at 37° C. but not stirred. About 0.5 g of sugar was added to each capsule.

The filled capsule was dropped into the water, which floated and moved to the wall of the flask. The time for complete release of the DiPac® sugar from the capsule was determined. The normalized time for release was calculated based on a nominal 100 micron thick coating, and the test was performed three times for each formulation. Table 11 summarizes the results of the release study.

TABLE 11

Content Release Times of Pullulan Capsules.

| Formulation | Average Capsule Wall Thickness (microns) | Release Time (sec) | Normalized Release Time (Sec) |
|---|---|---|---|
| Table 8; #1 | 140.0 ± 17.3 | 333.0 ± 80.9 | 239.3 ± 57.9 |
| Table 8; #2 | 103.3 ± 15.3 | 104.0 ± 32.0 | 102.0 ± 36.0 |
| Formula A | 113.3 ± 11.5 | 95.0 ± 21.0 | 83.3 ± 12.7 |

In a separate set of experiments, the same release test was performed on capsules from Formulations 3 and 4 from Table 8 and from Formula A (Table 9). Each formulation was tested 6-8 times. The results are summarized in Table 12. The normalized data was calculated using the thickness of the wall of the capsule.

TABLE 12

Content Release Times of Pullulan Capsules.

| Formulation | Average Capsule Wall Thickness (microns) | Release Time (sec) | Normalized Release Time (Sec) |
|---|---|---|---|
| Table 8; #3 | 87.5 ± 19.1 | 251.0 ± 109.5 | 276.0 ± 107.4 |
| Table 8; #4 | 63.8 ± 11.0 | 129.5 ± 49.0 | 177.2 ± 63.0 |
| Formula A | 116.3 ± 14.1 | 99.9 ± 23.5 | 83.9 ± 19.7 |

Example 10

Dissolution Study of Capsules in the Mouth

Capsules were prepared as described above with DiPac® and the time for the first release of DiPac® sugar noted along with the time for complete film dissolution of the capsule in the mouth was measured. Table 13 summarizes the results.

TABLE 13

Dissolution Study of Capsules in the Mouth.

| Formulation | Average Time for detection of DiPac® Sugar Release | Average Time for Complete Dissolution of capsule (Sec; n = 3) |
|---|---|---|
| Table 8; #1 | 30.3 ± 7.1 | 136.0 ± 23.3 |
| Table 8; #2 | 40.3 ± 14.2 | 165.3 ± 3.9 |
| Formula A | 11.3 ± 6.0 | 73.7 ± 11.0 |

The foregoing example shows that the preparation of capsules using the procedure described in U.S. Pat. No. 3,784,390 could not be prepared using the pin dipping procedure due to its low viscosity and lack of adhesion to the pins. Capsules could be prepared using a higher concentration of the gelatin-pullulan in the dipping solution and using multiple dippings. The most rapidly dissolving capsules were the capsules of the present invention followed by the capsules prepared with Gelatin Type B and the slowest were the Gelatin Type A capsules.

Example 11

Preparation of Enteric Coated Capsules of the Present Invention and CAPSUGEL Gelatin Capsules and Determination of Drug Release Times Caffeine was chosen at the marker drug for addition to the capsules. A mixture of 50 g of DiPac® Directly Compactable Sugar and 1.8 g of caffeine were mixed and each capsule (Formula A or CAPSUGEL® gelatin opaque, cream) was filled with approximately 518 mg of the mixture. The caps were put onto the capsule body (both capsules are #0 capsules) and were coated with Acryl-Eze® acrylic enteric coating system (Colorcon). Table 14 shows the enteric coating solution ingredients.

TABLE 14

Enteric Coating Solution

| Acryl-Eze ® Powder | 100 g |
| Water | 400 g |
| Antifoam A | 3 drops |

The coating solution was vigorously stirred and then stirred slowly overnight. The capsules were coated in a UniGlatt fluidized bed coater with center column. About 380 g of coating solution was applied onto six capsules of the present invention and six CAPSUGEL® capsules with 500 g of high-density polyethylene drops used as fillers for the coating operation. The capsules of the present invention showed an average of 70.5 mg of coating and the CAPSUGEL® capsules contained an average of 67.1 mg of coating.

TABLE 15

Capsule Coating Conditions

| | |
|---|---|
| Inlet temperature | 40° C. |
| Outlet temperature | 36-38° C. |
| Atomization air pressure | 1.2 bar |
| Coating rate | 5.5 g/min |

Release rate studies were performed using a USP dissolution paddle system at 50 rpm, 900 mL of Simulated Gastric Fluid (no enzymes, "SGF") and 900 mL of Simulated Intestinal Fluid (no enzymes, SIF) at 37° C. A continuous flow system was used to monitor the absorbance at 272 nm (caffeine absorbance) at 1-minute intervals over 3 hours. The capsules were placed into cylindrical cages (1 cm diameter×3 cm long) of 20-mesh stainless steel screen.

Release rate studies were performed using a USP dissolution paddle system at 37° C. The capsules were subjected to SGF for the first 2 hours and then the cages transferred to the SIF media.

Figure 4:
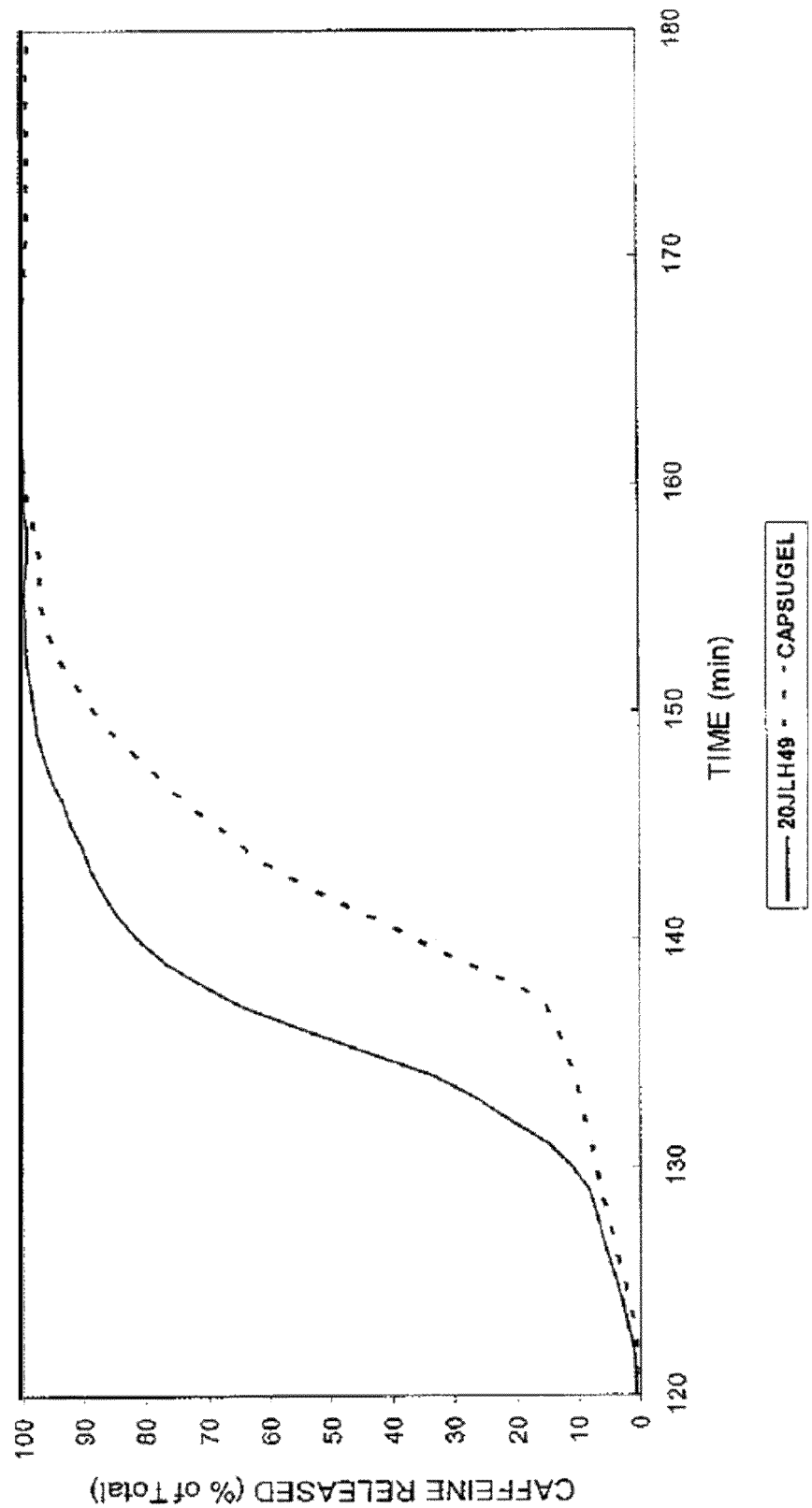
FIG. 4 shows the release of caffeine from enteric coated capsules of Example 11 (20JLH49) compared to commercial Capsugel® gelatin capsules that were also enteric coated.

Three runs for each capsule were made and the results are presented in FIG. 4 for the time the capsules were in SGF. No change in absorbance was observed for the two hour the capsules were in SGF, thereby demonstrating the integrity of the coatings.

The average time for caffeine to start to be released from the enteric coated capsules of the present invention is approximately 18 minutes sooner than the time for release from the CAPSUGEL® capsules.

Example 12

Capsule Disintegration Time: Comparison to Capsules of Prior Art

Capsules were prepared using the Formula A capsule formulation as described in Table 9, using pullulan (106.5 g), glycerin (10.65 g), polydextrose (10.65 g), maltose (10.65 g) and acesulfame K (1.065 g). Other capsule formulations were prepared using the same formulation except as noted. For example, the amount of maltose was varied, or the maltose was replaced with sorbitol or lactose where noted. Capsules were prepared using Formula B capsule formulation with pullulan (106.5 g), glycerin (10.65 g), polydextrose (10.65 g), and sorbitol (21.3 g). The empty capsules were stored in a plastic container in a 23° C., 56% relative humidity oven. Capsules were manufactured 1 week to 3 months prior to filling. Capsules were filled on the day disintegration studies were performed. The capsules were filled with mannitol (Mannogem 2080). The thickness of each body (3 measurements each) and cap (2 measurements each), weights of empty bodies and caps, and weights of filled capsules were measured. The USP disintegration method was used. The disintegration medium was 900 mL of water at 37° C., or 25° C., as noted. Breakthrough time was monitored visually by observation of the time the white mannitol granules were initially released from the capsule and floated in the disintegration medium. The disintegration time of six capsules was measured for each capsule formulation. Results are shown in Tables 16A, B and C.

TABLE 16A

Capsule Breakthrough Time at 37° C.

| | Formulation | | | | |
|---|---|---|---|---|---|
| Capsule | Pullulan Only Disintegration Break Through Time (sec) | Formula A Disintegration Break Through Time (sec) | 11.5% Glycerin* Disintegration Break Through Time (sec) | No Maltose Disintegration Break Through Time (sec) | 20% Maltose* Disintegration Break Through Time (sec) |
| 1 | 20 | 41 | 5 | 23 | 25 |
| 2 | 20 | 12 | 9 | 21 | 13 |
| 3 | 36 | 14 | 5 | 16 | 15 |
| 4 | 28 | 19 | 35 | 18 | 8 |
| 5 | 37 | 27 | 12 | 20 | 8 |
| 6 | 21 | 24 | 17 | 12 | 39 |
| Average | 27.00 | 22.83 | 13.83 | 18.33 | 18.00 |
| SD | 7.95 | 10.57 | 11.32 | 3.93 | 12.03 |

*% based on wt of Pullulan

TABLE 16B

Capsule Breakthrough Time at 37° C.

| | Formulation | | | | |
|---|---|---|---|---|---|
| Capsule | 10% Sorbitol* Disintegration Break Through Time (sec) | 10% Lactose* Disintegration Break Through Time (sec) | NP Capsules Disintegration Break Through Time (sec) | Gelatin Capsules Disintegration Break Through Time (sec) | HPMC Capsules Disintegration Break Through Time (sec) |
| 1 | 22 | 22 | 39 | 90 | 148 |
| 2 | 27 | 38 | 47 | 90 | 151 |
| 3 | 22 | 17 | 45 | 89 | 129 |
| 4 | 20 | 10 | 48 | 88 | 245 |

TABLE 16B-continued

Capsule Breakthrough Time at 37° C.

| | Formulation | | | | |
|---|---|---|---|---|---|
| Capsule | 10% Sorbitol* Disintegration Break Through Time (sec) | 10% Lactose* Disintegration Break Through Time (sec) | NP Capsules Disintegration Break Through Time (sec) | Gelatin Capsules Disintegration Break Through Time (sec) | HPMC Capsules Disintegration Break Through Time (sec) |
| 5 | 22 | 28 | 38 | 131 | 165 |
| 6 | 24 | 14 | 39 | 102 | 152 |
| Average | 22.83 | 21.50 | 42.67 | 98.33 | 165.00 |
| SD | 2.40 | 10.23 | 4.50 | 16.81 | 40.87 |

*% based on wt of Pullulan

TABLE 16C

Capsule Breakthrough Time at 37° C.

| Capsule | Formulation 20% Sorbitol* Formula B Disintegration Break Through Time (sec) |
|---|---|
| 1 | 7 |
| 2 | 7 |
| 3 | 12 |
| 4 | 12 |
| 5 | 10 |
| 6 | 7 |
| Average | 9.17 |
| SD | 2.48 |

*% based on wt of Pullulan

On average, HPMC capsules disintegrated in 2 minutes and 45 seconds, gelatin capsules disintegrated in 1 min 30 seconds, and Capsugel NPcaps® capsules (commercial pullulan capsules designed to mimic gelatin capsules) disintegrated in 43 seconds. The Formula A capsule average disintegration time was approximately 20 seconds with a range of 14-23 seconds. The Formula B capsule average disintegration time was 9.17 seconds with a range of 7-12 seconds. Capsules made of only pullulan with no other excipients added disintegrated on average at approximately 27 seconds.

A second disintegration was run at 25° C. using Formula A compared to the commercial Capsugel NPcaps® capsules. The disintegration time data at 25° C. and 37° C. for the Formula A capsule and the Capsugel NPcaps® capsules are shown in FIG. 2. At 25° C. and 37° C. the disintegration of the Formula A capsule was approximately twice as fast as the Capsugel NPcaps®.

Example 13

Capsule Dissolution: Comparison to Capsules of Prior Art

Capsules were prepared using the Formula A capsule formulation as described in Table 9, using pullulan (106.5 g), glycerin (10.65 g), polydextrose (10.65 g), maltose (10.65 g) and acesulfame K (1.065 g). The empty capsules were stored in a plastic container in a 23° C., 56% relative humidity oven. Capsules were manufactured 1 week to 3 months prior to testing. Capsules were filled with copper wire to weight capsules so they sank to the bottom of the dissolution vessel. The USP dissolution paddle method was used at 50 rpm. The dissolution medium was 900 mL of water at 37° C. Dissolution time was monitored by UV absorbance at 200 nm every 15 seconds with normalization against a blank at 200 nm. Data includes an average of three runs for Formula A capsules and two runs for Capsugel NPcaps® capsules. The data are shown in FIG. 3. The initial rate of dissolution was 30% per minute for the Formula A capsules and 6.9% per minute for the NP capsules. This is a factor of over 4 times faster for the Formula A capsules.

Example 14

Additional Capsule Shell Formulations

Additional capsule shell formulations comprising lactose, rather than maltose, and various amounts of glycerol were prepared by the method of Example 6 and are shown in Table 17.

TABLE 17

Capsule Shell Formulations with Lactose.

| | 8% Sorbitol/8% Glycerin/10% Lactose | | 8% Sorbitol/9% Glycerin/10% Lactose | |
|---|---|---|---|---|
| | g | % | g | % |
| Pullulan | 106.5 | 73.46 | 106.5 | 74.00 |
| Glycerin | 8.52 | 5.88 | 9.59 | 6.66 |
| Polydextrose | 10.65 | 7.35 | 10.65 | 7.40 |
| Sorbitol | 8.52 | 5.88 | 8.52 | 5.92 |
| Lactose | 10.65 | 7.35 | 8.52 | 5.92 |
| Na Benzoate | 0.1393 | 0.10 | 0.1393 | 0.10 |
| Total Solids | 144.9793 | 100 | 143.9143 | 100 |

Additional capsule shell formulations with various molecular weight polyvinyl alcohols (PVAs) were prepared by the method of Example 6, and are shown in Table 18. PVAs of three different MWs were employed. PVA-A refers to Spectrum Chemicals, polyvinyl alcohol, USP, P1180, 85-89% hydrolysis with viscosity of 4% solution @38.0 cps (est. MW~85,000-124,000; Med-High molecular weight (MW)); PVA-B refers to Sigma Aldrich, poly(vinyl) alcohol, 363081; 87-89% hydrolysis, MW=85,000-124,000 (Med MW); PVA-C refers to Sigma Aldrich poly(vinyl) alcohol, 363073, 87-89% hydrolysis, MW=31,000-50,000 (Low MW). PVA-A was used in the prior formulation examples.

TABLE 18

Capsule Shell Formulations with PVA of Various MW.

| | 10% PVA_C (g) | 10% PVA_C (%) | 10% PVA_B/10% Sorbitol (g) | 10% PVA_B/10% Sorbitol (%) | 5% PVA_B/8% Sorbitol/9% Glycerin/10% Lactose Formula C (g) | 5% PVA_B/8% Sorbitol/9% Glycerin/10% Lactose Formula C (%) |
|---|---|---|---|---|---|---|
| Water | 290 | — | 290 | — | 290 | — |
| Pullulan | 106.5 | 71.36 | 106.5 | 71.36 | 106.5 | 70.36 |
| Glycerin | 10.65 | 7.14 | 10.65 | 7.14 | 9.585 | 6.33 |
| Polydextrose | 10.65 | 7.14 | 10.65 | 7.14 | 10.65 | 7.04 |
| PVA_A | — | — | — | — | — | — |
| PVA_B | — | — | 10.65 | 7.14 | 5.325 | 3.52 |
| PVA_C | 10.65 | 7.14 | — | — | — | — |
| Maltose | 10.65 | 7.14 | — | — | — | — |
| Sorbitol | — | — | 10.65 | 7.14 | 8.52 | 5.63 |
| Lactose | — | — | — | — | 10.65 | 7.04 |
| Na Benzoate | 0.1385 | 0.09 | 0.1358 | 0.09 | 0.1358 | 0.09 |
| Total Solids | 149.2385 | 100 | 149.2358 | 100.00 | 151.3658 | 100.00 |

Example 15

Capsule Shell Formulations Comprising Solutol

Capsule shell formulations with the wetting agent Solutol were prepared with the materials shown in Tables 19A and 19B. Capsule shell formulations were prepared as disclosed in Example 6; except notably that formulations containing Solutol required heating to only about 50° C., rather than to above 60° C., in order to dissolve the pullulan. Capsule shells were prepared as described in Example 6. The term "Original" in Tables 19A and 19B refers to the formulation of Table 6.

TABLE 19A

Capsule Formulations with Solutol.

| | 20% Polydextrose/10% Sorbitol/10% Lactose* (g) | 20% Polydextrose/10% Sorbitol/10% Lactose* (%) | 20 g Polydextrose/8% Sorbitol/9% Glycerin/10% Lactose* (g) | 20 g Polydextrose/8% Sorbitol/9% Glycerin/10% Lactose* (%) | Original with 1.5% Solutol* Formula D (g) | Original with 1.5% Solutol* Formula D (%) | Original with 3.0% Solutol* Formula E (g) | Original with 3.0% Solutol* Formula E (%) |
|---|---|---|---|---|---|---|---|---|
| Water | 290 | — | 290 | — | 290 | — | 290 | — |
| Pullulan | 106.5 | 66.61 | 106.5 | 67.97 | 106.5 | 75.97 | 106.5 | 75.11 |
| Glycerin | 10.65 | 6.66 | 9.585 | 6.12 | 10.65 | 7.6 | 10.65 | 7.51 |
| Polydextrose | 21.3 | 13.32 | 21.3 | 13.59 | 106.5 | 7.6 | 10.65 | 7.51 |
| Maltose | — | — | — | — | 10.65 | 7.6 | 10.65 | 7.51 |
| Sorbitol | 10.65 | 6.66 | 8.52 | 5.44 | — | — | — | — |
| Lactose | 10.65 | 6.66 | 10.65 | 6.80 | — | — | — | — |
| Na Benzoate | 0.1358 | 0.08 | 0.1358 | 0.09 | 0.1358 | 0.10 | 0.1358 | 0.10 |
| Solutol | — | — | — | — | 1.605 | 1.14 | 3.21 | 2.29 |
| | 159.89 | 100.00 | 156.69 | 100.00 | 140.19 | 100.00 | 141.80 | 100.00 |

*wt % based on wt of Pullulan

TABLE 19B

Capsule Formulations with Solutol.

| | Original with 5% Sorbitol/5% Solutol*/No Maltose (g) | Original with 5% Sorbitol/5% Solutol*/No Maltose (%) | Original with 5% Solutol* (g) | Original with 5% Solutol* (%) | Original with 2.5% Solutol/2.5% Sorbitol* Formula F (g) | Original with 2.5% Solutol/2.5% Sorbitol* Formula F (%) | Original with 2.5% Solutol/5% Sorbitol* Formula G (g) | Original with 2.5% Solutol/5% Sorbitol* Formula G (%) |
|---|---|---|---|---|---|---|---|---|
| Water | 290 | — | 290 | — | 290 | — | 290 | — |
| Pullulan | 106.5 | 76.85 | 106.5 | 74.00 | 106.5 | 75.40 | 106.5 | 75.40 |
| Glycerin | 10.65 | 7.68 | 10.65 | 7.40 | 10.65 | 7.54 | 10.65 | 7.54 |
| Polydextrose | 10.65 | 7.68 | 10.65 | 7.40 | 10.65 | 7.54 | 10.65 | 7.54 |
| Maltose | — | — | 10.65 | 7.40 | 7.9875 | 5.65 | 5.325 | 3.77 |

TABLE 19B-continued

Capsule Formulations with Solutol.

|  | Original with 5% Sorbitol/5% Solutol*/No Maltose | | Original with 5% Solutol* | | Original with 2.5% Solutol/2.5% Sorbitol* Formula F | | Original with 2.5% Solutol/5% Sorbitol* Formula G | |
|---|---|---|---|---|---|---|---|---|
|  | (g) | (%) | (g) | (%) | (g) | (%) | (g) | (%) |
| Sorbitol | 5.325 | 3.84 | — | — | 2.6625 | 1.88 | 5.325 | 3.77 |
| Na Benzoate | 0.1358 | 0.10 | 0.1358 | 0.09 | 0.1358 | 0.10 | 0.1358 | 0.10 |
| Solutol | 5.325 | 3.84 | 5.325 | 3.70 | 2.6625 | 1.88 | 2.6625 | 1.88 |
|  | 138.56 | 100.00 | 143.92 | 100.00 | 141.25 | 100.00 | 141.25 | 100.00 |

*wt % based on wt of Pullulan

Example 16

Disintegration of Capsule Shell Formulations Comprising PVA-B or Solutol

Certain capsule shell formulations containing PVA-B or Solutol, from Examples 14 and 15, respectively, were prepared as described in Example 6. The capsule shells were filled with mannitol and disintegration experiments were performed by the USP disintegration method as described in Example 12. Disintegration times, corrected for capsule shell thickness, are shown in Table 20.

TABLE 20

Capsule Breakthrough Time at 37° C.

| | Formulation | | | | |
|---|---|---|---|---|---|
| Capsule | Formula C 5% PVA-B* Disintegration Break Through Time (sec) | Formula D 1.5% Solutol* Disintegration Break Through Time (sec) | Formula E 3.0% Solutol* Disintegration Break Through Time (sec) | Formula F 2.5% Solutol*/ 2.5% Sorbitol Disintegration Break Through Time (sec) | Formula G 2.5% Solutol*/ 5% Sorbitol Disintegration Break Through Time (sec) |
| 1 | 20 | 9 | 17 | 17 | 10 |
| 2 | 16 | 15 | 23 | 18 | 13 |
| 3 | 9 | 18 | 15 | 16 | 16 |
| 4 | 15 | 13 | 16 | 12 | 10 |
| 5 | 17 | 14 | 27 | 18 | 22 |
| 6 | 22 | 12 | 15 | 7 | 19 |
| Average | 17 | 14 | 19 | 15 | 15 |
| SD | 4.51 | 3.02 | 5.00 | 4.37 | 4.90 |

*% is wt % based on wt of Pullulan

The hard shell pullulan capsules comprising Solutol were surprisingly found to have improved integrity compared to other capsules, and to be slicker when cured, which helped impart ease of handling, ease of processing and improved mouth feel. Particularly preferred capsule formulations included the wetting agent Solutol and the dissolution enhancing agent sorbitol. Addition of sorbitol to the pullulan-Solutol capsules seemed to improve the malleability of the capsule. Remarkably, hard shell pullulan capsules comprising Solutol were found to be stable when stored in a closed container at room temperature and ambient humidity for 35 months. Empty capsules stored in such a manner could be opened without exhibiting brittleness or puckering after 35 months.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth herein and the drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. An orally dissolving hard shell capsule comprising pullulan, in an amount from 60 wt % to 80 wt % based on total capsule shell solids, polydextrose, a plasticizer, a dissolution enhancing agent and wetting agent macrogol 15 hydroxystearate.

2. The capsule of claim 1 comprising pullulan in an amount from about 65 to about 80 wt % based on total capsule shell solids.

3. The capsule of claim 1 wherein the wetting agent is present in an amount from about 1 wt % to about 10 wt % based on total capsule shell solids.

4. The capsule of claim 3 wherein the plasticizer is a polyol is selected from at least one of the group consisting of glycerol, propylene glycol, polyvinyl alcohol, sorbitol, poloxomers, and maltitol.

5. The capsule of claim 1 comprising plasticizer in an amount from about 0.1 wt % to about 20 wt % based on total capsule shell solids.

6. The capsule of claim 1 wherein the dissolution enhancing agent is selected from at least one of maltose, lactose, sorbitol, mannitol, gluconic acid lactone, xylitol, maltitol, and isomalt.

7. The capsule of claim 5 wherein the dissolution enhancing agent is selected from at least one of maltose, lactose, and sorbitol.

8. The capsule of claim 1 comprising dissolution enhancing agent in an amount from about 0.1 wt % to about 35 wt % based on total capsule shell solids.

9. The capsule of claim 1 further comprising up to about 5 wt % each of one or more selected from the group consisting of a sweetener, flavoring agent, and saliva inducing agent, based on total capsule shell solids.

10. The orally dissolving capsule comprising pullulan of claim 1, said capsule having an average normalized average breakthrough time of less than 30 seconds in an aqueous disintegration test at 37° C.

11. The capsule of claim 10 comprising about 70-80 wt % pullulan, about 5-10 wt % glycerin, about 5-10 wt % polydextrose, about 2-10 wt % maltose, about 1-5 wt % sorbitol and about 1-5 wt % macrogol 15 hydroxystearate, based on the total weight of the capsule shell solids.

* * * * *